US008420329B2

(12) United States Patent
Nakamura et al.

(10) Patent No.: US 8,420,329 B2
(45) Date of Patent: Apr. 16, 2013

(54) METHODS FOR DIAGNOSING OR TREATING PROSTATE CANCER

(75) Inventors: Yusuke Nakamura, Tokyo (JP); Hidewaki Nakagawa, Tokyo (JP); Takuya Tsunoda, Kanagawa (JP)

(73) Assignee: OncoTherapy Science, Inc., Kanagawa (JP)

( * ) Notice: Subject to any disclaimer, the term of this patent is extended or adjusted under 35 U.S.C. 154(b) by 0 days.

(21) Appl. No.: 13/130,284

(22) PCT Filed: Nov. 18, 2009

(86) PCT No.: PCT/JP2009/006201
§ 371 (c)(1),
(2), (4) Date: Aug. 17, 2011

(87) PCT Pub. No.: WO2010/058572
PCT Pub. Date: May 27, 2010

(65) Prior Publication Data
US 2011/0294123 A1      Dec. 1, 2011

Related U.S. Application Data

(60) Provisional application No. 61/199,964, filed on Nov. 20, 2008.

(51) Int. Cl.
*G01N 33/53* (2006.01)
(52) U.S. Cl.
USPC .......................................................... 435/7.1
(58) Field of Classification Search ........................ None
See application file for complete search history.

(56) References Cited

U.S. PATENT DOCUMENTS

| 7,727,714 B2 | 6/2010 | Nakamura et al. |
| 2010/0204060 A1 | 8/2010 | Nakamura et al. |

FOREIGN PATENT DOCUMENTS

| WO | 03/009814 A2 | 2/2003 |
| WO | WO 2005/019475 A2 | 3/2005 |
| WO | 2007/013479 A2 | 2/2007 |
| WO | WO 2007/013575 A2 | 2/2007 |

OTHER PUBLICATIONS

Law et al. (Experimental Cell Research VOl 314 available Mar. 4, 2008 p. 1823).*
Tockman et al (Cancer Res., 1992, 52:2711s-2718s).*
U.S. Appl. No. 13/224,102, filed Sep. 1, 2011, 82 pages.
Chang, A., et al., "A novel human cDNA highly homologous to the fish hormone stanniocalcin," *Mol Cell Endocrinol.*, vol. 112(2), pp. 241-247 (Aug. 11, 1995).
Feldman, B., et al., "The Development of Androgen-Independent Prostate Cancer," *Nat Rev Cancer*, vol. 1(1), pp. 34-45 (Oct. 2001).
Goo, Y., et al., "Stromal mesenchyme cell genes of the human prostate and bladder," *BMC Urol.*, vol. 5(17), pp. 1-11 (Dec. 12, 2005).

Gronberg, H., "Prostate cancer epidemiology," *Lancet*, vol. 361(9360), pp. 859-864 (Mar. 8, 2003).
Han, M., et al., "Era specific biochemical recurrence-free survival following radical prostatectomy for clinically localized prostate cancer," *J. Urol.*, vol. 166(2), pp. 416-419 (Aug. 2001).
Heeboll, S., et al., "SMARCC1 expression is upregulated in prostate cancer and positively correlated with tumor recurrence and dedifferentiation," *Histol Histopathol.*, vol. 23(9), pp. 1069-1076 (Sep. 2008).
Hsing, A., et al., "Trends and Patterns of Prostate Cancer: What Do They Suggest?," *Epidemiol Rev.*, vol. 23(1), pp. 3-13 (2001).
Ishibashi, K., et al., "Molecular Cloning of a Second Human Stanniocalcin Homologue (STC2)," *Biochem Biophys Res Commun.*, vol. 250(2), pp. 252-258 (Sep. 18, 1998).
Ito, D., et al., "Characterization of Stanniocalcin 2, a Novel Target of the Mammalian Unfolded Protein Response with Cytoprotective Properties," *Mol Cell Biol.*, vol. 24(21), pp. 9456-9469 (Nov. 2004).
Jellinek, D., et al., "Stanniocalcin 1 and 2 are secreted as phosphoproteins from human fibrosarcoma cells," *Biochem. J.*, Viol. 350, Pt. 2, pp. 453-461 (Sep. 1, 2000).
Law, A., et al., "Epigenetic and HIF-1 regulation of stanniocalcin-2 expression in human cancer cells," *Exp Cell Res.*, vol. 314(8), pp. 1823-1830 (May 1, 2008, Epub Mar. 8, 2008).
Liu, W., et al., "cDNA microarray analysis of pigment epithelium-derived factor-regulated gene expression profile in prostate carcinoma cells," *Int J Urol.*, vol. 16(3), pp. 323-328 (Mar. 2009, Epub Jan. 12, 2009).
Meyer, H., et al., "Identification of Stanniocalcin 2 as Prognostic Marker in Renal Cell Carcinoma," *Eur Urol.*, vol. 55(3), pp. 669-678 (Mar. 2009, Epub Apr. 9, 2008).
Scher, H., et al., "Biology of Progressive, Castration-Resistant Prostate Cancer: Directed Therapies Targeting the Androgen-Receptor Signaling Axis," *J Clin Oncol.*, vol. 23(32), pp. 8253-8261 (Nov. 10, 2005). Tamura, K., et al., Molecular Features of Hormone-Refractory Prostate Cancer Cells by Genome-Wide Gene Expression Profiles, *Cancer Res.*, vol. 67(11), pp. 5117-5125 (Jun. 1, 2007).
Tamura, K., et al., "Stanniocalcin 2 overexpression in castration-resistant prostate cancer and aggressive prostate cancer," *Cancer Sci.*, vol. 100(5), pp. 914-919 (May 2009, Epub Feb. 26, 2009).
True, L., et al., "A molecular correlate to the Gleason grading system for prostate adenocarcinoma," *Proc Natl Acad Sci USA*, vol. 103(29), pp. 10991-10996 (Jul. 18, 2006, Epub Jul. 7, 2006).
Varghese, R., et al., "Comparative Analysis of Mammalian Stanniocalcin Genes," *Endocrinology*, vol. 139(11), pp. 4714-4725 (Nov. 1998).
Wagner, G., et al., "Studies on the regulation and characterization of plasma stanniocalcin in rainbow trout," *Mol Cell Endocrinol.*, vol. 79(1-3), pp. 129-138 (Aug. 1991).

(Continued)

*Primary Examiner* — Sean Aeder
(74) *Attorney, Agent, or Firm* — Kilpatrick Townsend & Stockton LLP

(57) ABSTRACT

The present invention provides methods for detecting and/or diagnosing cancer through the determination of the expression level of the STC2 gene. The gene was discovered to discriminate cancer cells from normal cells. Furthermore, the present invention provides methods of screening for therapeutic agents useful in the treatment of cancer, methods for treating cancer. Moreover, the present invention provides double-stranded molecules targeting the STC2 gene, which are suggested to be useful in the treatment of cancer. The compositions and methods of the present invention find particular applicability to prostate cancer, more specifically, castration-resistant prostate cancer and aggressive prostate cancer.

3 Claims, 3 Drawing Sheets

OTHER PUBLICATIONS

Wagner, G., et al., "Calcium regulates stanniocalcin mRNA levels in primary cultured rainbow trout corpuscles of Stannius," *Mol Cell Endocrinol.,* vol. 99(2), pp. 315-322 (Mar. 1994).

Constantine, et al., "Use of GeneChip high-density oligonucleotide arrays for gene expression monitoring," *Life Science News, Amaersham Life Science,* 5 pages (Jan. 1, 1998).

Human Genome U95Av2, downloaded from http://www.affymetrix.com, 1 page (Oct. 2, 2002).

GeneChip Human Genome U133 Set, downloaded from http://www.affymetrix.com/support/technical/datasheets/hgu133_datasheet.pdf, 2 pages (Feb. 26, 2003).

U.S. Appl. No. 11/913,147, which is a U.S. National Stage of PCT/JP2006/314946, filed on Jul. 21, 2006, 134 pages.

* cited by examiner

Fig. 1A-C
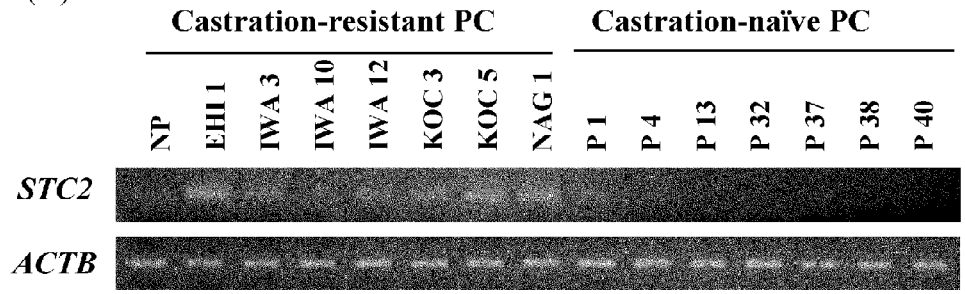
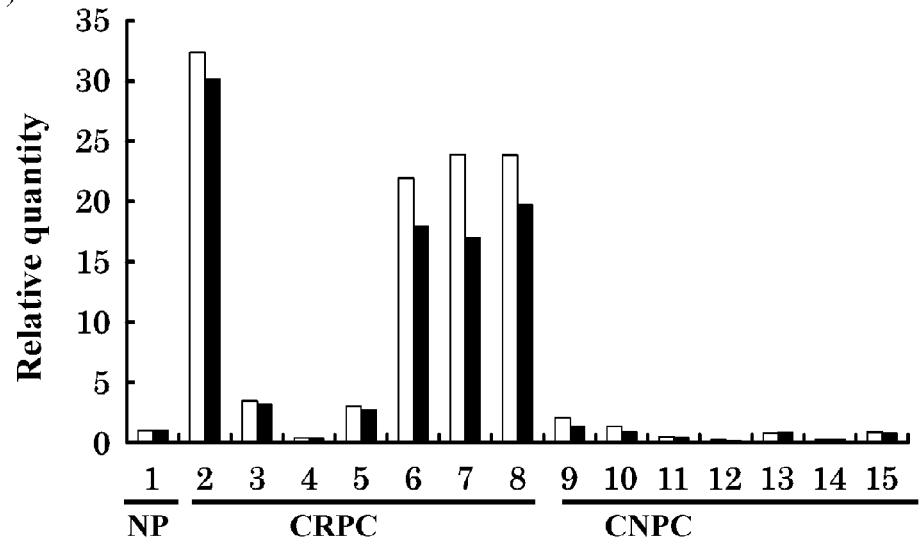
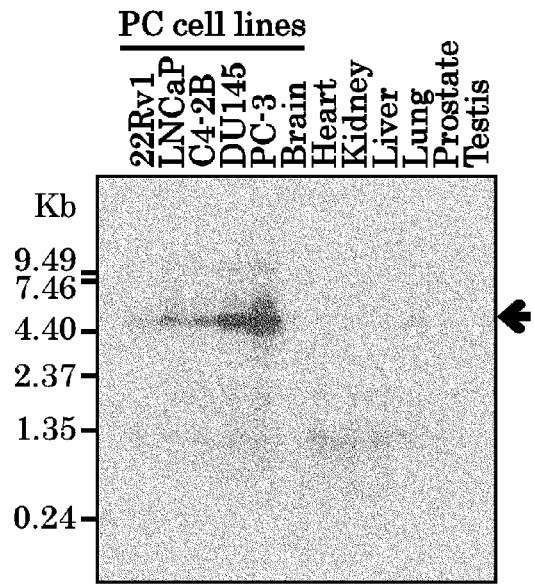

Fig. 1D-H
(D)
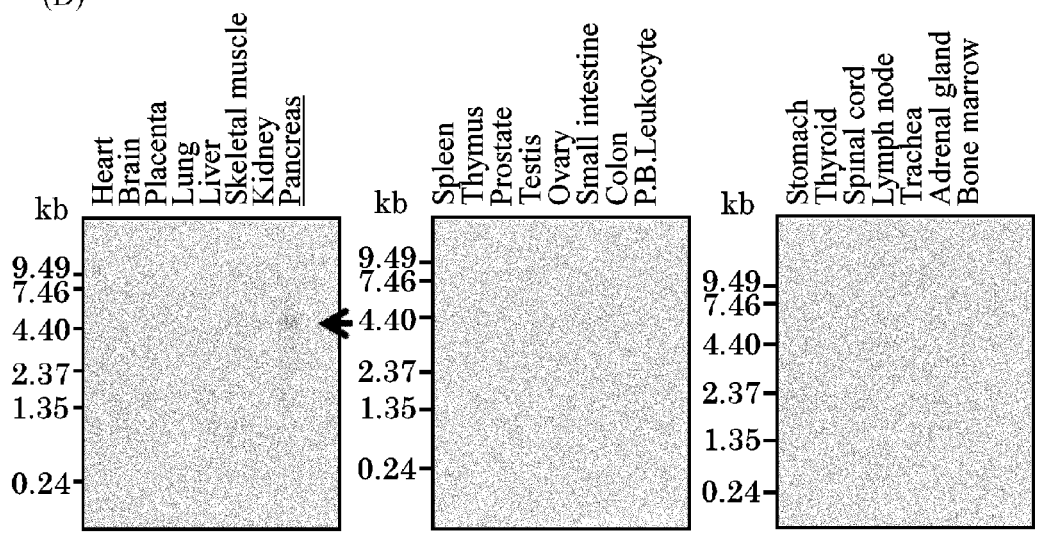
(E) CRPC
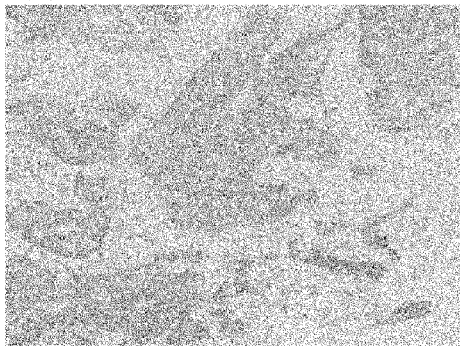
(F) CNPC with GS10
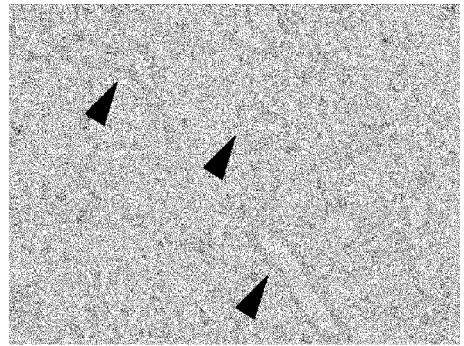
(G) CNPC with GS7
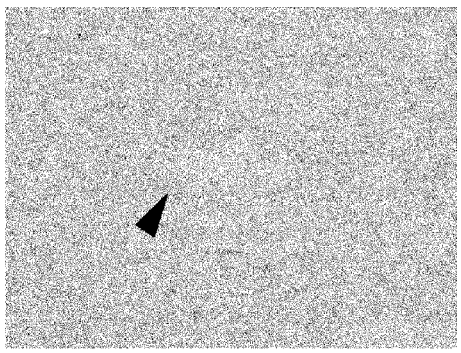
(H) immunohistochemical score
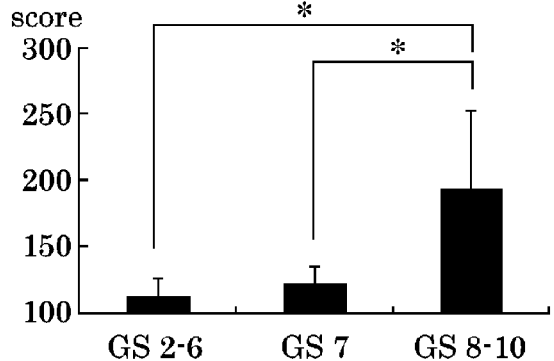

Fig. 2
(A)
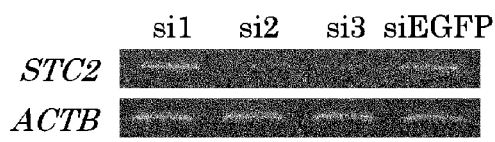
(B)
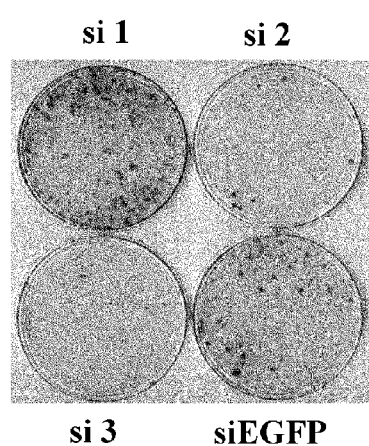
(C)
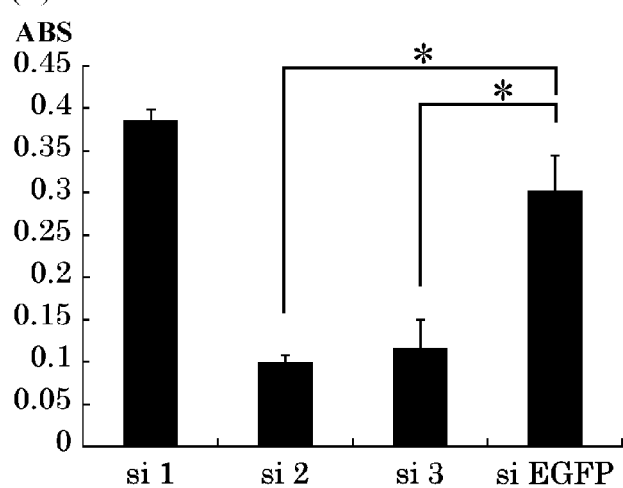
(D)
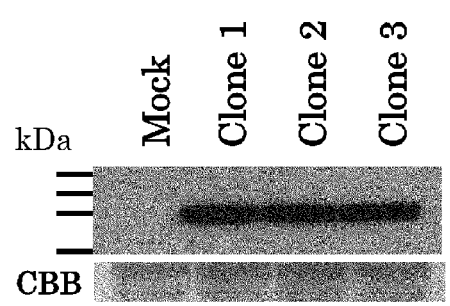
(E)
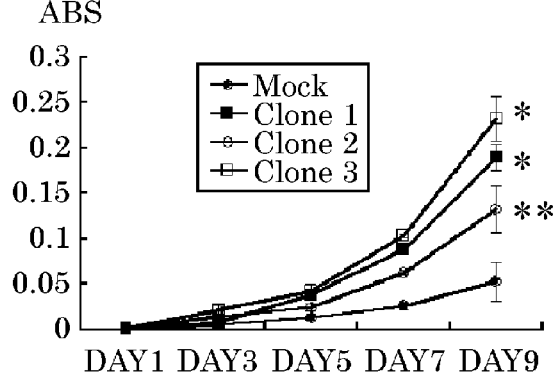

SEQUENCE LISTING

<160> NUMBER OF SEQ ID NOS: 12

<210> SEQ ID NO 1
<211> LENGTH: 20
<212> TYPE: DNA
<213> ORGANISM: Artificial
<220> FEATURE:
<223> OTHER INFORMATION: An artificially synthesized primer sequence for RT-PCR

```
<400> SEQUENCE: 1
ttggcttgac tcaggattta                                            20

<210> SEQ ID NO 2
<211> LENGTH: 20
<212> TYPE: DNA
<213> ORGANISM: Artificial
<220> FEATURE:
<223> OTHER INFORMATION: An artificially synthesized primer sequence for
      RT-PCR

<400> SEQUENCE: 2
atgctatcac ctcccctgtg                                            20

<210> SEQ ID NO 3
<211> LENGTH: 22
<212> TYPE: DNA
<213> ORGANISM: Artificial
<220> FEATURE:
<223> OTHER INFORMATION: An artificially synthesized primer sequence for
      RT-PCR

<400> SEQUENCE: 3
ttactccatg agccttcctt tg                                         22

<210> SEQ ID NO 4
<211> LENGTH: 23
<212> TYPE: DNA
<213> ORGANISM: Artificial
<220> FEATURE:
<223> OTHER INFORMATION: An artificially synthesized primer sequence for
      RT-PCR

<400> SEQUENCE: 4
tcctgttgcc taaatccgta gta                                        23

<210> SEQ ID NO 5
<211> LENGTH: 23
<212> TYPE: DNA
<213> ORGANISM: Artificial
<220> FEATURE:
<223> OTHER INFORMATION: An artificially synthesized primer sequence for
      preparing probe

<400> SEQUENCE: 5
aacatttacc attagagagg ggg                                        23

<210> SEQ ID NO 6
<211> LENGTH: 23
<212> TYPE: DNA
<213> ORGANISM: Artificial
<220> FEATURE:
<223> OTHER INFORMATION: An artificially synthesized primer sequence for
      preparing probe

<400> SEQUENCE: 6
cacatagaaa tgacactcct ccc                                        23

<210> SEQ ID NO 7
<211> LENGTH: 19
<212> TYPE: DNA
<213> ORGANISM: Artificial
<220> FEATURE:
<223> OTHER INFORMATION: An artificially synthesized oligonucleotide for
      siRNA

<400> SEQUENCE: 7
```

```
caactcttgt gagattcgg                                                  19
```

<210> SEQ ID NO 8
<211> LENGTH: 19
<212> TYPE: DNA
<213> ORGANISM: Artificial
<220> FEATURE:
<223> OTHER INFORMATION: An artificially synthesized oligonucleotide for
      siRNA

<400> SEQUENCE: 8

```
gacgaacagt ctgagtatt                                                  19
```

<210> SEQ ID NO 9
<211> LENGTH: 19
<212> TYPE: DNA
<213> ORGANISM: Artificial
<220> FEATURE:
<223> OTHER INFORMATION: An artificially synthesized oligonucleotide for
      siRNA

<400> SEQUENCE: 9

```
gcaggagctg gtattgtag                                                  19
```

<210> SEQ ID NO 10
<211> LENGTH: 19
<212> TYPE: DNA
<213> ORGANISM: Artificial
<220> FEATURE:
<223> OTHER INFORMATION: An artificially synthesized oligonucleotide for
      siRNA

<400> SEQUENCE: 10

```
gaagcagcac gacttcttc                                                  19
```

<210> SEQ ID NO 11
<211> LENGTH: 5361
<212> TYPE: DNA
<213> ORGANISM: Homo sapiens

<400> SEQUENCE: 11

```
tttctccttc cctccacggg ccgggtgaga aagtagccgg gggctatccc gacccggcgg     60
ttcttgggga gggggccgaa caagaaaagg gaggagatgg agataacttc cccggattta    120
gctttttgt ctttgttttt gttctcacca cttccatcgg atgactggag agtaaaaggg    180
aacccggagc ggggtggcga gcagcgcttt gagaaaatgc aggagtgtgt ttggagacgc    240
gtaaagttgc cttttcaagct ctggcctccg ggcacgcgat gctccgcggc gggctgactc    300
agggctgcct tgggcctccc tgccaccctc ctggaaatga tgcaagtcct gactgtcacc    360
tggatccctg cagcccagcc tggaatgcgt ctggattagg ggaaagacga gaaacgacac    420
tccaggtgtt gcacggccca ccaaagcggg aagatagggc agttgctcag accaaatact    480
gtatctagtg cttctgctcc tatcttcaat cgtggggttc tttttaatgc aaagtgtcac    540
aaggccagga attcccatgt gtgctcagtt ggcccacagc atcattgtgc ctaggaaact    600
gcttcaattt atcaagtcct ctgggctggg aatctcactg aattccaaac ggcggaaaga    660
ggaaactttc ccaacccgat gtgggtgtga cgcgagccag gggccccagg gacactgtcc    720
cagagcacac cgtccccctt taacagcaac tggagcttgg attcgctctt atattgtaca    780
gtccttcga ccattgccct ggagcacccg cacacgcgca cgcatctccg gccgcgctca    840
cacacactca tacacacgca cgcaaacgcg tggccgccgc caggtcggca actttgtccg    900
gcgctcccag cggcgctcgg cttcctcctg tagtagttga gcgcaggccc cgcctccgg    960
```

```
ccgtgttgtc aaaagggccg gggtctcgga ttggtccagc cgccgggaca acacctgctc    1020
gactccttca ttcaagtgac accagagctt ccagggatat ttgaggcacc atccctgcca    1080
ttgccgggca ctcgcggcgc tgctaacggc ctggtcacat gctctccgga gagctacggg    1140
agggcgctgg gtaacctcta tccgagccgc ggccgcgagg aggagggaaa aggcgagcaa    1200
aaaggaagag tgggaggagg aggggaagcg cgaaggagg aagaggagga ggaggaagag     1260
gggagcacaa aggatccagg tctcccgacg ggaggttaat accaagaacc atgtgtgccg    1320
agcggctggg ccagttcatg accctggctt tggtgttggc cacctttgac ccggcgcggg    1380
ggaccgacgc caccaaccca cccgagggtc cccaagacag gagctcccag cagaaaggcc    1440
gcctgtccct gcagaataca gcggagatcc agcactgttt ggtcaacgct ggcgatgtgg    1500
ggtgtggcgt gtttgaatgt ttcgagaaca actcttgtga gattcggggc ttacatggga    1560
tttgcatgac ttttctgcac aacgctggaa aatttgatgc ccagggcaag tcattcatca    1620
aagacgcctt gaaatgtaag gcccacgctc tgcggcacag gttcggctgc ataagccgga    1680
agtgcccggc catcagggaa atggtgtccc agttgcagcg ggaatgctac ctcaagcacg    1740
acctgtgcgc ggctgcccag gagaacaccc gggtgatagt ggagatgatc catttcaagg    1800
acttgctgct gcacgaaccc tacgtggacc tcgtgaactt gctgctgacc tgtggggagg    1860
aggtgaagga ggccatcacc cacagcgtgc aggttcagtg tgagcagaac tggggaagcc    1920
tgtgctccat cttgagcttc tgcaccctcg ccatccagaa gcctcccacg gcgcccccg     1980 agcgccagcc ccaggtggac agaaccaagc tctccagggc ccaccacggg aagcaggac     2040 atcacctccc agagcccagc agtagggaga ctggccgagg tgccaagggt gagcgaggta    2100
gcaagagcca cccaaacgcc catgcccgag gcagagtcgg gggccttggg gctcagggac    2160
cttccggaag cagcgagtgg gaagacgaac agtctgagta ttctgatatc cggaggtgaa    2220
atgaaaggcc tggccacgaa atctttcctc cacgccgtcc atttttcttat ctatggacat    2280 tccaaaacat ttaccattag agagggggga tgtcacacgc aggattctgt ggggactgtg    2340
gacttcatcg aggtgtgtgt tcgcggaacg gacaggtgag atggagaccc ctggggccgt    2400 gggtctcag gggtgcctgg tgaattctgc acttacacgt actcaaggga gcgcgcccgc     2460
gttatcctcg tacctttgtc ttcttttccat ctgtggagtc agtgggtgtc ggccgctctg    2520 ttgtgggga ggtgaaccag ggagggggcag ggcaaggcag ggccccaga gctgggccac     2580 acagtgggtg ctgggcctcg ccccgaagct tctggtgcag cagcctctgg tgctgtctcc    2640
gcggaagtca gggcggctgg attccaggac aggagtgaat gtaaaaataa atatcgctta    2700
gaatgcagga aagggtgga gaggaggcag gggccgaggg ggtgcttggt gccaaactga     2760
aattcagttt cttgtgtggg gccttgcggt tcagagctct tggcgagggt ggagggagga    2820
gtgtcatttc tatgtgtaat ttctgagcca ttgtactgtc tgggctgggg gggacactgt    2880
ccaagggagt ggccctatg agtttatatt ttaaccactg cttcaaatct cgatttcact     2940
ttttttattt atccagttat atctacatat ctgtcatcta aataaatggc tttcaaacaa    3000
agcaactggg tcattaaaac cagctcaaag ggggtttaaa aaaaaaaac cagcccatcc     3060 tttgaggctg attttctttt tttttaagtt ctatttaaa agctatcaaa cagcgacata     3120
gccatacatc tgactgcctg acatggactc ctgcccactt gggggaaacc ttatacccag    3180
aggaaaatac acacctgggg agtacatttg acaaatttcc cttaggattt cgttatctca    3240
ccttgaccct cagccaagat tggtaaagct gcgtcctggc gattccagga gacccagctg    3300
gaaacctggc ttctccatgt gaggggatgg gaaaggaaag aagagaatga agactactta    3360
```

```
gtaattccca tcaggaaatg ctgaccttt  acataaaatc aaggagactg ctgaaaatct    3420
ctaagggaca ggattttcca gatcctaatt ggaaatttag caataaggag aggagtccaa    3480
ggggacaaat aaaggcagag agaagagaca gaactaaaaa tacgaggaaa ggagagtgag    3540
gattttcatt aaaagtctca gcagtgggtt tcttgggtta tttaaaacat cacctaaata    3600
ggccttttct tcctaattgg ccatcaaatt aaagcctatc ctttctcaag caggagctgg    3660
tattgtaggg agtggccggg tattctgggc tgggctcttc tggagtaggg ggtcagcaaa    3720
cattgtctgc aaagggccag atactgaatc cagtactttc agtttggcga gccgtgaggt    3780
ctctgtcgaa actactcaac tctgccgtcc tagcacaaaa gcagccatag acaacacaca    3840
aacgagaggg cttggctccc ttccaggaag atttatttaa caggctccca gctgaatttc    3900
actcacagga cacagtttac tgatctctgt tctagtgagt gggtcaaaaa gcatatgcat    3960
ccttatccgt caactcatca gctcttcctc aaggcaacct gaggccagac accaagaaac    4020
caagcgtatc tgctctaaaa tgacttgttc ctggggaatg ccttcaacca aaacacagct    4080
agtatttcta tgccccaaat ccaatcccag tctttcatga tccatgccgg cggttgggtg    4140
gggaggggaa tcattggttg ggggaaggga ggaaacccca cctccagccc ccgccaccgg    4200
gctccctggg cacccagcaa gatctggggc tgcagagaac agaagagctg gtgcacttaa    4260
tccagctctg cccttggggg gaggaggacc tgtgtgtcag gctctgccat gggaacgagt    4320
gtaaaccgtg gctgtctcct gcagtgagcc accgcggcag gcacgttgac tgttttactg    4380
acatcactca aaagctaaag caataacatt ctcctgcgtt gctgagtcag ctgttcattt    4440
gtccgccagc tcctggactg gatgtgtgaa aggcatcaca tttccatttt cctccgtgta    4500
aatgttttat gtgttcgcct actgatccca ttcgttgctt ctattgtaaa tatttgtcat    4560
ttgtatttat tatctctgtg ttttccccct aaggcataaa atggtttact gtgttcattt    4620
gaacccattt actgatctct gttgtatatt tttcatgcca ctgctttgtt ttctcctcag    4680
aagtcgggta gatagcattt ctatcccatc cctcacgtta ttggaagcat gcaacagtat    4740
ttattgctca gggtcttctg cttaaaactg aggaaggtcc acattcctgc aagcattgat    4800
tgagacattt gcacaatcta aaatgtaagc aaagtagtca ttaaaaatac accctctact    4860
tgggctttat actgcataca aatttactca tgagccttcc tttgaggaag gatgtggatc    4920
tccaaataaa gatttagtgt ttattttgag ctctgcatct taacaagatg atctgaacac    4980
ctctcctttg tatcaataaa tagccctgtt attctgaagt gagaggacca agtatagtaa    5040
aatgctgaca tctaaaacta aataaataga aaacaccagg ccagaactat agtcatactc    5100
acacaaaggg agaaatttaa actcgaacca agcaaaaggc ttcacggaaa tagcatggaa    5160
aaacaatgct tccagtggcc acttcctaag gaggaacaac cccgtctgat ctcagaattg    5220
gcaccacgtg agcttgctaa gtgataatat ctgtttctac tacggattta ggcaacagga    5280
cctgtacatt gtcacattgc attattttc ttcaagcgtt aataaagtt ttaaataaat    5340 ggcaaaaaaa aaaaaaaaa a                                                5361
```

<210> SEQ ID NO 12
<211> LENGTH: 302
<212> TYPE: PRT
<213> ORGANISM: Homo sapiens

<400> SEQUENCE: 12

Met Cys Ala Glu Arg Leu Gly Gln Phe Met Thr Leu Ala Leu Val Leu
1               5                   10                  15

-continued

```
Ala Thr Phe Asp Pro Ala Arg Gly Thr Asp Ala Thr Asn Pro Pro Glu
             20                  25                  30

Gly Pro Gln Asp Arg Ser Ser Gln Gln Lys Gly Arg Leu Ser Leu Gln
         35                  40                  45

Asn Thr Ala Glu Ile Gln His Cys Leu Val Asn Ala Gly Asp Val Gly
     50                  55                  60

Cys Gly Val Phe Glu Cys Phe Glu Asn Asn Ser Cys Glu Ile Arg Gly
 65                  70                  75                  80

Leu His Gly Ile Cys Met Thr Phe Leu His Asn Ala Gly Lys Phe Asp
                 85                  90                  95

Ala Gln Gly Lys Ser Phe Ile Lys Asp Ala Leu Lys Cys Lys Ala His
            100                 105                 110

Ala Leu Arg His Arg Phe Gly Cys Ile Ser Arg Lys Cys Pro Ala Ile
            115                 120                 125

Arg Glu Met Val Ser Gln Leu Gln Arg Glu Cys Tyr Leu Lys His Asp
        130                 135                 140

Leu Cys Ala Ala Ala Gln Glu Asn Thr Arg Val Ile Val Glu Met Ile
145                 150                 155                 160

His Phe Lys Asp Leu Leu Leu His Glu Pro Tyr Val Asp Leu Val Asn
                165                 170                 175

Leu Leu Leu Thr Cys Gly Glu Glu Val Lys Glu Ala Ile Thr His Ser
            180                 185                 190

Val Gln Val Gln Cys Glu Gln Asn Trp Gly Ser Leu Cys Ser Ile Leu
        195                 200                 205

Ser Phe Cys Thr Ser Ala Ile Gln Lys Pro Pro Thr Ala Pro Pro Glu
    210                 215                 220

Arg Gln Pro Gln Val Asp Arg Thr Lys Leu Ser Arg Ala His His Gly
225                 230                 235                 240

Glu Ala Gly His His Leu Pro Glu Pro Ser Ser Arg Glu Thr Gly Arg
                245                 250                 255

Gly Ala Lys Gly Glu Arg Gly Ser Lys Ser His Pro Asn Ala His Ala
            260                 265                 270

Arg Gly Arg Val Gly Gly Leu Gly Ala Gln Gly Pro Ser Gly Ser Ser
        275                 280                 285

Glu Trp Glu Asp Glu Gln Ser Glu Tyr Ser Asp Ile Arg Arg
    290                 295                 300
```

METHODS FOR DIAGNOSING OR TREATING PROSTATE CANCER

PRIORITY

The present application is a U.S. National Stage Application of PCT/JP2009/006201, filed Nov. 18, 2009, which claims the benefit of U.S. Provisional Application No. 61/199,964, filed Nov. 20, 2008, the entire contents of which are incorporated by reference herein in their entirety.

TECHNICAL FIELD

1. Technical Field

The present invention relates to the field of biological science, more specifically to the field of cancer diagnosis and treatment. In particular, the present invention relates to methods for detecting and diagnosing prostate cancer as well as methods for treating and preventing prostate cancer. Moreover, the present invention relates to methods for screening for a candidate compound for treating and/or preventing prostate cancer. The present invention further relates to double-stranded molecules that reduce or inhibit the expression of STC2 and uses thereof.

2. Background Art

Prostate cancer (PC) is the most common malignancy in males and the second leading cause of cancer-related deaths in the United States and Europe, and frequency of PC has been increasing significantly in most developed countries probably due to prevalent western-style life-style and the explosion of the aging population (NPL 1:Gronberg H, Lancet 2003, 361, 859-64, and NPL 2: Hsing A W and Devesa S S, Epidemiol Rev 2001, 23:3-13). Surgical and radiation therapies are effective to the localized disease, but nearly 30% of treated PC patients still suffer from the relapse of the disease (NPL 3:Feldman B J and Feldman D, Nat Rev Cancer 2001, 1, 34-45, NPL 4:Scher H I and Sawyers C L, J Clin Oncol 2006, 23, 8253-61, and NPL 5:Han M, et al., J Urol 2001, 166, 416-9). Most of the patients with relapsed or advanced disease respond well to androgen-ablation therapy (medical or surgical castration) because PCs are usually androgen-dependent at a relatively early stage. However, they often acquire castration-resistant phenotype that progresses aggressively and ultimately leads to the death of PC patients. Hence, development of new therapies based on the molecular mechanisms of prostate carcinogenesis or castration-resistant PC (CRPC) is urgently and eagerly required.

With that goal in mind, the present inventors previously performed genome-wide cDNA microarray analysis of CRPC cells and Castration-naive PC (CNPC) cells purified from clinical PC tissues by means of microdissection and identified dozens of genes whose expression levels were evidently increased in CRPC cells and/or CNPC cells, as compared to normal prostatic epithelial cells (NPL 6:Tamura K, et al., Cancer Res 2007, 67, 5117-5125). However, to date, genes useful for diagnosing and treating CRPC have not been identified.

Both castration-naive prostate cancers (CNPCs) with high Gleason score, and castration-resistant prostate cancers (CRPCs) respond poorly to androgen-ablation therapy and have highly aggressive behavior and thus are associated with poor prognosis. True et al. demonstrated a significant association between high levels of monoamine oxidase A (MAOA) expression and high-grade (Gleason patterns 4 and 5) PCs (NPL 7:True L, et al. PNAS 103, 10991-6, 2006) and Heeboll et al. revealed an increased expression of SMARCC1 protein in PC and a positive correlation with tumor dedifferentiation, progression, metastasis and time to recurrence (NPL 8:Heeboll S, et al., Histol Histopathol 2008, 23, 1069-76). However, to date, candidate secreted proteins correlated with Gleason score 8-10 have not been reported.

Accordingly, an objective of the present invention is to provide a new biomarker and new therapeutic strategies against PCs, in particular, CRPCs and aggressive PCs with high Gleason score. As discussed in detail herein, analysis of genome-wide expression profiles of PC cells suggest that the molecular target, STC2, is such a marker, having utility in the both the treatment and diagnosis of prostate cancer.

Stanniocalcin (STC) was first identified as a glycoprotein hormone secreted from specific endocrine glands (corpuscle of Stannius) in the kidney region of bony fish that is involved in calcium and phosphate homeostasis (NPL 9:Wagner G F, et al., Mol Cell Endocrinol 1991, 79, 129-38, and NPL 10:Wagner G F and Jaworski E, Mol Cell Endocrinol 1994, 99, 315-22). STC is released into the blood in response to rising serum calcium levels to regulate the $Ca^{2+}$ and phosphate uptake in different target organs (NPL 9:Wagner G F, et al., Mol Cell Endocrinol 1991, 79, 129-38, and NPL 10:Wagner G F and Jaworski E, Mol Cell Endocrinol 1994, 99, 315-22). In mammals that lack a specific corpuscle of stannius gland, two related mammalian genes have been identified, STC1 and STC2, both of which are predicted to be secreted glycosylated proteins (NPL 11:Chang A C, et al., Mol Cell Endocrinol 1995, 112, 241-7, and NPL 12:Ishibashi K, et al. Biochem Biophys Res Commun 1998, 250, 252-8). However, their physiological or pathological functions in human beings and human cancers have not been clearly elucidated, and their receptor binding partners have not yet identified.

Recent reports suggested that HIF-1 could regulate STC2 expression (NPL 13:Law A Y, et al., Exp Cell Res 2008, 314, 1823-30). In addition, a proportion of renal cancers have been observed to over-express STC2 and, in turn, correlated with aggressiveness and poor prognosis of renal cancer (NPL 14:Meyer H A, et al., Eur Urol 2008 Apr. 9). Another in-vitro study suggested that STC2 could potentially protect the cells from various cell stresses, especially ER stress (NPL 15:Ito D, et al., Mol Cell Biol 2004, 9456-69). However, whether STC2 is associated with PC progression is completely unknown, and possibility of targeting STC2 function or activity itself is yet to be known.

CITATION LIST

Non Patent Literature

[NPL 1] Gronberg H, Lancet 2003, 361, 859-64
[NPL 2] Hsing A W and Devesa S S, Epidemiol Rev 2001, 23:3-13
[NPL 3] Feldman B J and Feldman D, Nat Rev Cancer 2001, 1, 34-45
[NPL 4] Scher H I and Sawyers C L, J Clin Oncol 2006, 23, 8253-61
[NPL 5] Han M, et al., J Urol 2001, 166, 416-9
[NPL 6] Tamura K, et al., Cancer Res 2007, 67, 5117-5125
[NPL 7]
[NPL 7] True L, et al. PNAS 103, 10991-6, 2006
[NPL 8] Heeboll S, et al., Histol Histopathol 2008, 23, 1069-76
[NPL 9] Wagner G F, et al., Mol Cell Endocrinol 1991, 79, 129-38
[NPL 10] Wagner G F and Jaworski E, Mol Cell Endocrinol 1994, 99, 315-22
[NPL 11] Chang A C, et al., Mol Cell Endocrinol 1995, 112, 241-7

[NPL 12] Ishibashi K, et al. Biochem Biophys Res Commun 1998, 250, 252-8
[NPL 13] Law A Y, et al., Exp Cell Res 2008, 314, 1823-30
[NPL 14] Meyer H A, et al., Eur Urol 2008 Apr. 9
[NPL 15] Ito D, et al., Mol Cell Biol 2004, 9456-69

SUMMARY OF INVENTION

The present invention relates to the identification of STC2 as a molecular target useful in PC treatment and diagnosis. The STC2 protein finds particular utility as a molecular target for development of novel treatments for PC. Preferred PCs targeted by the prevent invention are CRPC and aggressive PC.

Accordingly, it is an object of the present invention to provide a method for diagnosing or determining a predisposition to PC in a subject by determining the expression level of the STC2 gene in a subject-derived biological sample, such as tissue, blood, or serum. An increase in the level of expression of the gene as compared to a normal control level indicates that the subject suffers from or is at risk of developing PC. The normal control level may be the expression level of the STC2 gene detected in a normal healthy tissue, blood, or serum of an individual or population known to be free from PC.

Alternatively, expression level of the STC2 gene in a sample can be compared to a cancerous control level of the STC2 gene. A similarity between the expression level of a sample and the cancerous control level indicates that the subject suffers from or is at risk of developing PC. The cancerous control level may be the expression level of the STC2 gene detected in the cancerous tissue, blood, or serum of an individual or population known to be suffering from PC.

It is another object of the present invention to provide a kit for diagnosing PC, such a kit minimally containing a reagent that measures the expression level of the STC2 gene in a subject-derived biological sample.

It is a further object of the present invention to provide methods for identifying agents that bind to the STC2 protein or inhibit the activity of the STC2 protein, such methods involving the steps of contacting the STC2 polypeptide with a test agent and determining the binding between the polypeptide and the test agent or a biological activity of the polypeptide. The test agent binding the polypeptide or suppressing a biological activity of the polypeptide may be used to reduce symptoms of PC.

The present invention also provides methods for identifying agents that inhibit the expression or activity of the STC2 protein, such method involving the steps of contacting a cell expressing the STC2 protein with a test agent and determining the expression level of the STC2 gene or the activity of the gene product, the STC2 protein. A decrease in the expression level of the gene or an activity of its gene product as compared to a control level in the absence of the test compound indicates that the test compound may be used to reduce symptoms of PC.

Furthermore, the present invention provides methods for identifying agents that inhibit the transcription of the STC2 gene, such methods involving the steps of contacting a test compound with the cell introduced with a vector that contains the transcriptional regulatory region of the STC2 gene and a reporter gene expressed under the control of the transcriptional regulatory region and determining the expression level or activity of the reporter gene. A decrease in the expression level of the gene or an activity of its gene product as compared to a control level in the absence of the test compound indicates that the test compound may be used to reduce symptoms of PC.

It is yet a further object of the present invention to provide double-stranded molecules and vectors encoding such molecules, both of which find utility in the treatment of PC. The double-stranded molecules include a sense strand and an antisense strand complementary thereto, hybridized to each other to form the double-stranded molecule and inhibit expression of the gene and cell proliferation when introduced into a cell expressing the STC2 gene. Preferably, the sense strand includes the sequence corresponding to a target sequence of SEQ ID NO:8 or 9.

Another aspect of the present invention relates to compositions for treating PC containing at least one of those siRNAs that inhibits cell proliferation of a cell expressing STC2 gene and methods for treating or preventing PC that includes the step of administering to a subject those compositions. The antisense polynucleotide or siRNA can be provided as a vector expressing those.

One advantage of the methods and kits described herein is that the disease may be identified prior to detection of overt clinical symptoms of PC. Another advantage of the methods and compositions described herein is that novel therapeutic approach with fewer adverse effect may be provided.

Other features and advantages of the present invention will be apparent from the following detailed description, and from the claims. To that end, it will be understood by those skilled in the art that one or more aspects of this invention can meet certain objectives, while one or more other aspects can meet certain other objectives. Each objective may not apply equally, in all its respects, to every aspect of this invention. As such, the preceding objects can be viewed in the alternative with respect to any one aspect of this invention. These and other objects and features of the invention will become more fully apparent when the following detailed description is read in conjunction with the accompanying figures and examples. However, it is to be understood that both the foregoing summary of the invention and the following detailed description are of a preferred embodiment, and not restrictive of the invention or other alternate embodiments of the invention.

BRIEF DESCRIPTION OF DRAWINGS

Various aspects and applications of the present invention will become apparent to the skilled artisan upon consideration of the brief description of the figures and the detailed description of the present invention and its preferred embodiments that follows:

[FIG. 1A-C] FIG. 1 demonstrates the over-expression of STC2 in CRPC cells and immunohistochemical analysis in PC tissues. Part (A) depicts the results of semi-quantitative RT-PCR validating STC2 over-expression in the microdissected CRPC cells as compared to CNPC cells and normal prostatic epithelial (NP) cells, which were also microdissected. ACTB was used to quantify the each of cDNA contents. Part (B) depicts the results of real-time quantitative RT-PCR demonstrating over-expression of STC2 transcript in CRPC cells (samples 2-8) as compared to that of CNPC cells (samples 9-15) and NP cells (sample 1). ACTB was used to quantify each of the cDNA contents, and the relative quantity (Y-axis) was calculated so that the expression in NP cells was one. Real-time quantitative RT-PCR was carried out duplicated for each sample (white and black columns). Part (C) depicts the results of Northern blot analysis demonstrating a high level of STC2 expression in five PC cell lines (lane 1-5), as compared to adult normal organs, including brain, heart, kidney, liver, lung, prostate and testis (lanes 6-12) wherein its expression is barely detectable.

[FIG. 1D-H] Part (D) depicts the results of multiple tissue Northern blot analysis demonstrating that STC2 was expressed only in normal pancreas, with no or very low expression of STC2 in adult normal organs. P. B. leukocyte means peripheral blood leukocyte. The length of STC2 transcript was about ~5.4 kb. Parts (E)-(H) demonstrate the immunoreactivity with anti-STC2 antibody observed in CRPC and CNPC with Gleason score 10 tissues examined, with strong positive immunostaining exhibited in the cytoplasm of PC cells. Part (E) is a representative picture of CRPC (×200), part (F) is a representative picture of CNPC with Gleason score 10 (×200), and part (G) is a representative picture of CNPC with Gleason score 7 (×200). Adjacent normal prostatic epithelium revealed very weak or no signal for STC2 (F and G; arrowheads). Part (H) depicts the relationship between STC2 immunohistochemical score and Gleason score in CNPCs. (*p<0.003, Mann-Whitney's U-test with Bonferroni method).

[FIG. 2] FIG. 2 demonstrates the knockdown of STC2 expression by siRNA attenuated PC cell viability and the promotion of cancer cell growth by STC2 over-expression. Part (A) depicts the knockdown effect of siRNA on STC2 in PC-3 cells. Semi-quantitative RT-PCR was performed using cells transfected with each of shRNA-expressing vectors to STC2 (si1-3) as well as a negative control vector (siEGFP). ACTB was used to quantify RNAs. Part (B) depicts the results of a colony formation assay of PC-3 cells transfected with each of indicated shRNA-expressing vectors to STC2 (si1-3) and a negative control vector (siEGFP). Cells were visualized with 0.1% crystal violet staining after 14-day incubation with Geneticin. Part (C) depicts the results of MTT assay of each of PC-3 cells transfected with indicated siRNA-expressing vectors to STC2 (si1-3) and a negative control vector (siEGFP). Each average is plotted with error bars indicating SD (standard deviation) after 10-day incubation with Geneticin. ABS on Y-axis means absorbance at 490 nm, and at 630 nm as reference, measured with a microplate reader. These experiments were carried out in triplicate (*P<0.01, Students' t-test). Part (D) depicts the results of Western blot analysis with anti-HA-tag antibody, demonstrating that three stable transformats (Clones 1-3) constitutively expressed an exogenous STC2. Mock was the 22Rv1-mock clone mixture. CBB stain served as a loading control. Part (E) depicts the in-vitro growth curve calculated by MTT assay, showing that three stable transformants (Clones 1-3) grew more rapidly than the 22Rv1-mock clone mixture (*P<0.01, **P<0.05, Students' t-test). ABS on Y-axis means absorbance at 490 nm, and at 630 nm as reference, measured with a microplate reader.

DESCRIPTION OF EMBODIMENTS

Although any methods and materials similar or equivalent to those described herein can be used in the practice or testing of embodiments of the present invention, the preferred methods, devices, and materials are now described. However, before the present materials and methods are described, it is to be understood that the present invention is not limited to the particular sizes, shapes, dimensions, materials, methodologies, protocols, etc. described herein, as these may vary in accordance with routine experimentation and optimization. It is also to be understood that the terminology used in the description is for the purpose of describing the particular versions or embodiments only, and is not intended to limit the scope of the present invention which will be limited only by the appended claims.

The disclosure of each publication, patent or patent application mentioned in this specification is specifically incorporated by reference herein in its entirety. However, nothing herein is to be construed as an admission that the invention is not entitled to antedate such disclosure by virtue of prior invention.

In case of conflict, the present specification, including definitions, will control. In addition, the materials, methods, and examples are illustrative only and not intended to be limiting.

DEFINITION

The words "a", "an", and "the" as used herein mean "at least one" unless otherwise specifically indicated.

The term "biological sample" refers to a whole organism or a subset of its tissues, cells or component parts (e.g., body fluids, including but not limited to blood, mucus, lymphatic fluid, synovial fluid, cerebrospinal fluid, saliva, amniotic fluid, amniotic cord blood, urine and semen). "Biological sample" further refers to a homogenate, lysate, extract, cell culture or tissue culture prepared from a whole organism or a subset of its cells, tissues or component parts, or a fraction or portion thereof. Lastly, "biological sample" refers to a medium, such as a nutrient broth or gel in which an organism has been propagated, which contains cellular components, such as proteins or polynucleotides.

The term "castration-resistant prostate cancer (CRPC)" refers to cancers that are tolerant to androgen-ablation therapy (castration). As used herein, the term "CRPC" includes androgen-independent phenotype that has been termed hormone-refractory prostate cancers (HRPCs).

The terms "isolated" and "purified" used in relation with a substance (e.g., polypeptide, antibody, polynucleotide, etc.) indicates that the substance is substantially free from at least one substance that may else be included in the natural source. Thus, an isolated or purified antibody refers to antibodies that are substantially free of cellular material such as carbohydrate, lipid, or other contaminating proteins from the cell or tissue source from which the protein (antibody) is derived, or substantially free of chemical precursors or other chemicals when chemically synthesized. The term "substantially free of cellular material" includes preparations of a polypeptide in which the polypeptide is separated from cellular components of the cells from which it is isolated or recombinantly produced. Thus, a polypeptide that is substantially free of cellular material includes preparations of polypeptide having less than about 30%, 20%, 10%, or 5% (by dry weight) of heterologous protein (also referred to herein as a "contaminating protein"). When the polypeptide is recombinantly produced, it is also preferably substantially free of culture medium, which includes preparations of polypeptide with culture medium less than about 20%, 10%, or 5% of the volume of the protein preparation. When the polypeptide is produced by chemical synthesis, it is preferably substantially free of chemical precursors or other chemicals, which includes preparations of polypeptide with chemical precursors or other chemicals involved in the synthesis of the protein less than about 30%, 20%, 10%, 5% (by dry weight) of the volume of the protein preparation. That a particular protein preparation contains an isolated or purified polypeptide can be shown, for example, by the appearance of a single band following sodium dodecyl sulfate (SDS)-polyacrylamide gel electrophoresis of the protein preparation and Coomassie Brilliant Blue staining or the like of the gel. In a preferred embodiment, antibodies and polypeptides of the present invention are isolated or purified. An "isolated" or "purified" nucleic acid molecule, such as a cDNA molecule, can be substantially free of other cellular material, or culture medium when produced by recombinant techniques, or substantially free of chemical precursors or other chemicals when chemically synthesized. The terms "polypeptide", "peptide", and "protein" are used interchangeably herein to refer to a polymer of amino acid residues. The terms apply to amino acid polymers in which one or more amino acid residue is a modified residue, or a non-naturally occurring residue, such as an artificial chemical mimetic of a corresponding naturally occurring amino acid, as well as to naturally occurring amino acid polymers.

The term "amino acid" refers to naturally occurring and synthetic amino acids, as well as amino acid analogs and amino acid mimetics that similarly functions to the naturally occurring amino acids. Naturally occurring amino acids are those encoded by the genetic code, as well as those modified after translation in cells (e.g., hydroxyproline, gamma-carboxyglutamate, and O-phosphoserine). The phrase "amino acid analog" refers to compounds that have the same basic chemical structure (an alpha carbon bound to a hydrogen, a carboxy group, an amino group, and an R group) as a naturally occurring amino acid but have a modified R group or modified backbones (e.g., homoserine, norleucine, methionine, sulfoxide, methionine methyl sulfonium). The phrase "amino acid mimetic" refers to chemical compounds that have different structures but similar functions to general amino acids.

Amino acids may be referred to herein by their commonly known three letter symbols or the one-letter symbols recommended by the IUPAC-IUB Biochemical Nomenclature Commission.

The terms "gene", "polynucleotides", "oligonucleotide", "nucleotides", "nucleic acids", and "nucleic acid molecules" are used interchangeably unless otherwise specifically indicated and are similarly to the amino acids referred to by their commonly accepted single-letter codes. Similar to the amino acids, they encompass both naturally-occurring and non-naturally occurring nucleic acid polymers. The polynucleotide, oligonucleotide, nucleotides, nucleic acids, or nucleic acid molecules may be composed of DNA, RNA or a combination thereof.

Unless otherwise defined, the terms "cancer" refers to cancers over-expressing the STC2 gene, more particularly prostate cancers such as CRPC, more particularly castration-resistant prostate cancer.

The STC2 gene or STC2 protein:

The present invention is based in part on the discovery of elevated expression of the STC2 gene in cells from patients of PCs. The expression of the gene was discovered to be particularly elevated in CRPC. An exemplified nucleotide sequence of human STC2 gene is shown in SEQ ID NO: 11 and is also available as GenBank Accession No. NM_003714. Another nucleotide sequence data for the human STC2 gene is available as GenBank Accession No. AK075406. Herein, the STC2 gene encompasses the human STC2 gene as well as those of other animals including non-human primate, mouse, rat, dog, cat, horse, and cow but are not limited thereto, and includes allelic mutants and genes found in other animals as corresponding to the STC2 gene.

An exemplified amino acid sequence encoded the human STC2 gene is shown in SEQ ID NO: 12 and is also available as GenBank Accession No. NP_003705. In the present invention, the polypeptide encoded by the STC2 gene is referred to as "STC2", and sometimes as "STC2 polypeptide" or "STC2 protein".

According to an aspect of the present invention, functional equivalents are also included in the STC2 polypeptide. Herein, a "functional equivalent" of a protein is a polypeptide that has a biological activity equivalent to the protein. Namely, any polypeptide that retains the biological ability of the STC2 protein may be used as such a functional equivalent in the present invention. Such functional equivalents include those wherein one or more amino acids are substituted, deleted, added, or inserted to the natural occurring amino acid sequence of the STC2 protein. Alternatively, the polypeptide may be one that includes an amino acid sequence having at least about 80% homology (also referred to as sequence identity) to the sequence of the respective proteins, more preferably at least about 90% to 95% homology, even more preferably 96% to 99% homology. In other embodiments, the polypeptide can be encoded by a polynucleotide that hybridizes under stringent conditions to the naturally occurring nucleotide sequence of the STC2 gene.

The phrase "stringent (hybridization) conditions" refers to conditions under which a nucleic acid molecule will hybridize to its target sequence, typically in a complex mixture of nucleic acids, but not detectably to other sequences. Stringent conditions are sequence-dependent and will vary in different circumstances. Longer sequences hybridize specifically at higher temperatures. An extensive guide to the hybridization of nucleic acids is found in Tijssen, Techniques in Biochemistry and Molecular Biology-Hybridization with Nucleic Probes, "Overview of principles of hybridization and the strategy of nucleic acid assays" (1993). Generally, stringent conditions are selected to be about 5-10 degrees C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times of background, preferably 10 times of background hybridization. Exemplary stringent hybridization conditions can be as following: 50% formamide, 5×SSC, and 1% SDS, incubating at 42 degrees C., or, 5×SSC, 1% SDS, incubating at 65 degrees C., with wash in 0.2×SSC, and 0.1% SDS at 50 degrees C.

In the context of the present invention, a condition of hybridization for isolating a DNA encoding a polypeptide functionally equivalent to the human STC2 protein can be routinely selected by a person skilled in the art. For example, hybridization may be performed by conducting pre-hybridization at 68 degrees C. for 30 min or longer using "Rapid-hyb buffer" (Amersham LIFE SCIENCE), adding a labeled probe, and warming at 68 degrees C. for 1 hour or longer. The following washing step can be conducted, for example, in a low stringent condition. An exemplary low stringent condition may include 42 degrees C., 2×SSC, 0.1% SDS, preferably 50 degrees C., 2×SSC, 0.1% SDS. High stringency conditions are often preferably used. An exemplary high stringency condition may include washing 3 times in 2×SSC, 0.01% SDS at room temperature for 20 min, then washing 3 times in 1×SSC, 0.1% SDS at 37 degrees C. for 20 min, and washing twice in 1×SSC, 0.1% SDS at 50 degrees C. for 20 min. However, several factors, such as temperature and salt concentration, can influence the stringency of hybridization and one skilled in the art can suitably select the factors to achieve the requisite stringency.

In general, modification of one, two or more amino acids in a protein will not influence the function of the protein. In fact, mutated or modified proteins (i.e., peptides composed of an amino acid sequence in which one, two, or several amino acid residues have been modified through substitution, deletion, insertion and/or addition) have been known to retain the original biological activity (Mark et al., Proc Natl Acad Sci USA 81: 5662-6 (1984); Zoller and Smith, Nucleic Acids Res 10:6487-500 (1982); Dalbadie-McFarland et al., Proc Natl Acad Sci USA 79: 6409-13 (1982)). Accordingly, one of skill in the art will recognize that individual additions, deletions, insertions, or substitutions to an amino acid sequence that alter a single amino acid or a small percentage of amino acids or those considered to be "conservative modifications", wherein the alteration of a protein results in a protein with similar functions, are acceptable in the context of the instant invention. Thus, in one embodiment, the peptides of the present invention may have an amino acid sequence wherein one, two or even more amino acids are added, inserted, deleted, and/or substituted in the STC2 sequence.

So long as the activity the protein is maintained, the number of amino acid mutations is not particularly limited. However, it is generally preferred to alter 5% or less of the amino acid sequence. Accordingly, in a preferred embodiment, the number of amino acids to be mutated in such a mutant is generally 30 amino acids or less, preferably 20 amino acids or less, more preferably 10 amino acids or less, more preferably 5 or 6 amino acids or less, and even more preferably 3 or 4 amino acids or less.

An amino acid residue to be mutated is preferably mutated into a different amino acid in which the properties of the amino acid side-chain are conserved (a process known as conservative amino acid substitution). Examples of properties of amino acid side chains are hydrophobic amino acids (A, I, L, M, F, P, W, Y, V), hydrophilic amino acids (R, D, N, C, E, Q, G, H, K, S, T), and side chains having the following functional groups or characteristics in common: an aliphatic side-chain (G, A, V, L, I, P); a hydroxyl group containing side-chain (S, T, Y); a sulfur atom containing side-chain (C, M); a carboxylic acid and amide containing side-chain (D, N, E, Q); a base containing side-chain (R, K, H); and an aromatic containing side-chain (H, F, Y, W). Conservative substitution tables providing functionally similar amino acids are well known in the art. For example, the following eight groups each contain amino acids that are conservative substitutions for one another:

1) Alanine (A), Glycine (G);
2) Aspartic acid (d), Glutamic acid (E);
3) Aspargine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cystein (C), Methionine (M) (see, e.g., Creighton, Proteins 1984).

Such conservatively modified polypeptides are included in the present STC2 protein. However, the present invention is not restricted thereto and the STC2 protein includes nonconservative modifications so long as they retain at least one biological activity of the STC2 protein. Furthermore, the modified proteins do not exclude polymorphic variants, interspecies homologues, and those encoded by alleles of these proteins.

Moreover, the STC2 gene of the present invention encompasses polynucleotides that encode such functional equivalents of the STC2 protein. In addition to hybridization, a gene amplification method, for example, the polymerase chain reaction (PCR) method, can be utilized to isolate a polynucleotide encoding a polypeptide functionally equivalent to the STC2 protein, using a primer synthesized based on the sequence information of the protein encoding DNA. Polynucleotides and polypeptides that are functionally equivalent to the human STC2 gene and protein, respectively, normally have a high homology to the originating nucleotide or amino acid sequence of. "High homology" typically refers to a homology of 40% or higher, preferably 60% or higher, more preferably 80% or higher, even more preferably 90% to 95% or higher, even more preferably 96% to 99% or higher. The homology of a particular polynucleotide or polypeptide can be determined by following the algorithm in "Wilbur and Lipman, Proc Natl Acad Sci USA 80: 726-30 (1983)".

I. Diagnosing Cancer:

I-1. Method for Diagnosing Cancer or a Predisposition for Developing Cancer

According to the present invention, the expression of the STC2 gene was found to be specifically elevated in patients with PC, more particularly, in CRPC and aggressive PC (see Example 2). Accordingly, the STC2 genes identified herein as well as their transcription and translation products find diagnostic utility as a marker for PC and by measuring the expression of the STC2 gene in a subject-derived biological sample, PC can be diagnosed. More particularly, the present invention provides a method for detecting, diagnosing and/or determining the presence of or a predisposition for developing cancer, more particularly PC in a subject by determining the expression level of the STC2 gene in the subject.

In the context of the present invention, the term "diagnosing" is intended to encompass predictions and likelihood analysis. The present method is intended to be used clinically in making decisions concerning treatment modalities, including therapeutic intervention, diagnostic criteria such as disease stages, and disease monitoring and surveillance for cancer. According to the present invention, an intermediate result for examining the condition of a subject may also be provided. Such intermediate result may be combined with additional information to assist a doctor, nurse, or other practitioner to diagnose that a subject suffers from the disease.

Alternatively, the present invention may be used to detect cancerous cells in a subject-derived tissue or biological sample and provide a doctor with useful information to diagnose that the subject suffers from the disease.

A subject to be diagnosed by the present method is preferably a mammal. Exemplary mammals include, but are not limited to, human, non-human primate, mouse, rat, dog, cat, horse, and cow.

It is preferred to collect a biological sample from a subject to be diagnosed to perform the diagnosis. Any biological material can be used as the biological sample for the determination so long as it contains the objective transcription or translation product of the STC2 gene. The biological samples include, but are not limited to, bodily tissues, especially some of a prostatic tissue and bodily fluids, such as blood, sputum, semen, prostatic fluid and urine. Preferably, the biological sample contains a cell population including an epithelial cell, more preferably a prostate epithelial cell derived from tissue suspected to be cancerous. Further, if necessary, cells may be purified from an obtained bodily tissues and fluids, and then used as a biological sample.

According to the present invention, the expression level of the STC2 gene is determined in a subject-derived biological sample. The expression level can be determined at the transcription (nucleic acid) product level, using methods known in the art. For example, the mRNA of the STC2 gene may be quantified using a probe by hybridization methods (e.g., Northern hybridization). The detection may be carried out on a chip or an array. The use of an array is preferable for detecting the expression level of a plurality of genes (e.g., various cancer specific genes) including the present STC2 gene. Those skilled in the art can prepare such probes utilizing the sequence information of the STC2 gene (for example, the sequence shown in SEQ ID NO: 11; GenBank Accession No. NM_018423 or GenBank Accession No. AK075406). For example, the cDNA of the STC2 gene may be used as the probes. If necessary, the probe may be labeled with a suitable label, such as dyes and isotopes, and the expression level of the gene may be detected as the intensity of the hybridized labels.

Furthermore, the transcription product of the STC2 gene may be quantified using primers by amplification-based detection methods (e.g., RT-PCR). Such primers can also be prepared based on an available sequence information of the gene. For example, the primers used in Example 1 (SEQ ID NOs: 3 and 4) may be employed for the detection by RT-PCR, but the present invention is not restricted thereto.

Specifically, a probe or primer used for the present method hybridizes under stringent, moderately stringent, or low stringent conditions to the mRNA of the STC2 gene. As used herein, the phrase "stringent (hybridization) conditions" refers to conditions under which a probe or primer will hybridize to its target sequence, but to no other sequences. Stringent conditions are sequence-dependent and will be different under different circumstances. Specific hybridization of longer sequences is observed at higher temperatures than shorter sequences. Generally, the temperature of a stringent condition is selected to be about 5 degrees C. lower than the thermal melting point ($T_m$) for a specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present at excess, at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30 degrees C. for short probes or primers (e.g., 10 to 50 nucleotides) and at least about 60 degrees C. for longer probes or primers. Stringent conditions may also be achieved with the addition of destabilizing agents, such as formamide.

Alternatively, the translation product may be detected for the diagnosis of the present invention. For example, the quantity of the STC2 protein may be determined. A method for determining the quantity of the protein as the translation product includes immunoassay methods that use an antibody specifically recognizing the protein. The antibody may be monoclonal or polyclonal. Furthermore, any fragment or modification (e.g., chimeric antibody, scFv, Fab, F(ab')$_2$, Fv, etc.) of the antibody may be used for the detection, so long as the fragment retains the binding ability to the STC2 protein. Methods to prepare these kinds of antibodies for the detection of proteins are well known in the art, and any method may be employed in the present invention to prepare such antibodies and equivalents thereof.

As another method to detect the expression level of the STC2 gene based on its translation product, the intensity of staining may be observed via immunohistochemical analysis using an antibody against the STC2 protein. Namely, the observation of strong staining indicates increased presence of the protein and at the same time high expression level of the STC2 gene.

Especially, STC2 protein is secreted protein. Therefore, by measuring the level of STC2 in subject-derived blood samples, the occurrence of or a predisposition to develop prostate cancer expressing STC2 in a subject can be determined. In the present invention, any blood samples may be used for determining the level of STC2 so long as either the gene or the protein of STC2 can be detected in the samples. Preferably, the blood samples include whole blood, serum, and plasma. The method of determining the level of STC2 was known to those skilled in the art, like ELISA, especially sandwich method.

Furthermore, the translation product may be detected based on its biological activity. The STC2 gene have been isolated as one of the mammalian gene related to STC gene that has been known to regulate calcium and phosphate uptake in different target organs (Wagner G F, et al., Mol Cell Endocrinol 1991, 79, 129-38, and Wagner G F and Jaworski E, Mol Cell Endocrinol 1994, 99, 315-22) and it was reported that the STC2 protein inhibited the phosphate uptake of a kidney cell line (Ishibashi K, et al., Biochem Biophys Res Commun 1998, Sep. 18; 250(2), 258-8). Furthermore, according to the present invention, the translation product of STC2 gene has an ability to promote PC cell growth. Thus, the inhibiting activity against the phosphate uptake of a kidney cell line or the cancer cell growth promoting activity may be used as an index of the STC2 protein existing in the biological sample.

Moreover, in addition to the expression level of the STC2 gene, the expression level of other cancer-associated genes, for example, genes known to be differentially expressed in CRPC, may also be determined to improve the accuracy of the diagnosis.

The expression level of the STC2 gene in a biological sample can be considered to be increased if it increases from the control level of the STC2 gene by, for example, 10%, 25%, or 50%; or increases to more than 1.1 fold, more than 1.5 fold, more than 2.0 fold, more than 5.0 fold, more than 10.0 fold, or more.

The control level may be determined at the same time with the test biological sample by using a sample(s) previously collected and stored from a subject/subjects whose disease state (cancerous or non-cancerous) is/are known. Alternatively, the control level may be determined by a statistical method based on the results obtained by analyzing previously determined expression level(s) of the STC2 gene in samples from subjects whose disease state are known. Furthermore, the control level can be a database of expression patterns from previously tested cells. Moreover, according to an aspect of the present invention, the expression level of the STC2 gene in a biological sample may be compared to multiple control levels, which control levels are determined from multiple reference samples. It is preferred to use a control level determined from a reference sample derived from a tissue type similar to that of the patient-derived biological sample. Moreover, it is preferred, to use the standard value of the expression levels of the STC2 gene in a population with a known disease state. The standard value may be obtained by any method known in the art. For example, a range of mean plus/minus 2 S.D. or mean plus/minus 3 S.D. may be used as standard value.

In the context of the present invention, a control level determined from a biological sample that is known to be non-cancerous or cancer-free is called "normal control level". On the other hand, if the control level is determined from a cancerous biological sample, it will be called "cancerous control level".

When the expression level of the STC2 gene in a biological sample derived from a subject is increased compared to the normal control level or is similar to the cancerous control level, the subject may be diagnosed to be suffering from or at a risk of developing cancer. Furthermore, in the case where the expression levels of multiple cancer-related genes are compared, a similarity in the gene expression pattern between the sample and the reference that is cancerous indicates that the subject is suffering from or at a risk of developing cancer. Difference between the expression levels of a test biological sample and the control level can be normalized to the expression level of control nucleic acids, e.g. housekeeping genes whose expression levels are known not to differ depending on the cancerous or non-cancerous state of the cell. Exemplary housekeeping genes include, but are not limited to, beta actin, glyceraldehyde 3 phosphate dehydrogenase, and ribosomal protein P1.

Alternatively, the present invention provides a method for detecting or identifying prostate cancer cells in a subject-derived prostate tissue sample, said method including the step of determining the expression level of the STC2 gene in a subject-derived biological sample, wherein an increase in said expression level as compared to a normal control level of said gene indicates the presence or suspicion of cancer cells in the tissue.

Such result may be combined with additional information to assist a doctor, nurse, or other healthcare practitioner in diagnosing a subject as afflicted with the disease. In other words, the present invention may provide a doctor with useful information to diagnose a subject as afflicted with the disease. For example, according to the present invention, when there is doubt regarding the presence of prostate cancer cells in the tissue obtained from a subject, clinical decisions can be reached by considering the expression level of the STC2 gene, plus a different aspect of the disease including tissue pathology, levels of known tumor marker(s) in blood, and clinical course of the subject, etc. For example, some well-known diagnostic prostate tumor markers in blood is PSA. Namely, in this particular embodiment of the present invention, the outcome of the gene expression analysis serves as an intermediate result for further diagnosis of a subject's disease state. In another embodiment, the present invention provides a method for detecting a diagnostic marker of prostate cancer, said method including the step of detecting the expression of the STC2 gene in a subject-derived biological sample as a diagnostic marker of prostate cancer.

According to the present invention, prostate cancer cells can be diagnosed or detected. In preferable embodiments, the presence of CRPC or aggressive prostate cancer cells within a prostate tissue may be diagnosed or detected. In the present invention, aggressive prostate cancer refers to prostate cancer having Gleason score (Gleason tumor grade) of 8 or more. For example, prostate cancer with Gleason score 8-10 is considered to be aggressive prostate cancer.

The present invention reveals that the immunostaining intensity of the STC2 polypeptide in a biological sample derived from a prostate cancer patient is increased as compared to the control level. Therefore, the present invention also provides a method of correlating the immunostaining intensity of the STC2 polypeptide with the presence of prostate cancer including the steps as follows:

(a) determining or evaluating the immunostaining intensity of the STC2 polypeptide in a biological sample derived from a subject; and (b) correlating the immunostaining intensity of step (a) with the presence of prostate cancer.

In a preferred embodiment, the present invention provides a method of correlating the immunostaining intensity of the STC2 polypeptide with the presence of prostate cancer including the steps as follows:

(a) determining or evaluating the immunostaining intensity of the STC2 polypeptide in a biological sample derived from a subject;

(b) comparing the immunostaining intensity of step (a) with a control level; and (c) correlating an increase in the immunostaining intensity determined in step (b) as compared to the control level to the presence of prostate cancer.

Any biological samples described above are suitable for correlating the immunostaining intensity of the STC2 polypeptide with the presence of prostate cancer. In a preferred embodiment of the present invention, a biological sample may be fixed chemically or physically. For example, the formalin fixed biological sample is preferable for evaluating the immunostaining intensity of the STC2 polypeptide Alternatively, in case where an electron microscope is used, the biological sample can be fixed with a glutaraldehyde or osmium teraoxide.

In the context of the present invention, a tissue derived from a subject is preferable as the biological sample. For example, a tissue in the present invention is a prostate tissue, more preferably prostate epithelial tissue. In order for determining or evaluating the immunostaining intensity, in general, sections may be prepared from tissue samples. Methods for preparing the tissue section are well known in the art. For example, methods for preparing a frozen section, unfrozen section, or paraffin section are known.

Preferably, prostate cancer of the present invention is CRPC, CNPC, or an aggressive prostate cancer, more preferably CRPC, CNPC, or an aggressive prostate cancer with Gleason score 8-10.

Immunostaining intensity can be determined or evaluated with a labeled anti-STC2 antibody. For example, anti-STC2 antibody may be labeled with enzymes. In preferable embodiment, the following enzymes are suitable for the anti-STC2 antibody labeling;

alkaline phosphatase,
horseradish peroxidase,
beta-galactosidase, or
beta-glucosidase.

When the anti-STC2 antibody is labeled with an enzyme, the antibody can be detected or measured with a substrate which reacts with the enzyme to generate detectable signals. Substrates generating detectable signals including color change, accumulation of dyes, or pigments having color fluorescence, or luminescence are well known. These detectable signals may be observed with a light microscope or fluorescence microscope.

Alternatively, the antibody may be labeled with fluorescent substances. In case where a fluorescent substance is labeled with the antibody, the antibody bound to the biological sample may be detected or measured by a fluorescence microscope. In preferable embodiments, fluorescein isothiocyanate (FITC), or rhodamine is suitable as the label in the present invention.

In another embodiment of the present invention, the antibody may also be labeled with a gold colloid. When the anti-STC2 antibody is labeled with gold colloid, the bound antibody may be detected or measured with a light microscope or electron microscope.

In an immunohistological analysis, the number of strongly or highly positive immunostained cells may be counted to determine or evaluate immunostaining intensity of the biological sample. In particular, the immunostaining intensity may determined or evaluated by comparing numbers of cells having positive and/or negative staining in the biological sample with control.

The immunostaining intensity of the biological sample may also be estimated or assessed in some grades. For example, three or more grades scoring or classifying of the immunostaining intensity may be applied to the present invention. In particular, the positive staining of the anti-STC2 antibody may be defined as follows:

(1) variable weak cytoplasmic staining, and (2) segmental and apical granular cytoplasmic staining, and (3) diffuse continuous and intense cytoplasmic staining.

According to such score, cell population of each score is determined. Further, in order for easy comparison, the sum of the population of cells with each score may be calculated for each sample as described previously (Ashida S, et al., Clin Cancer Res 2006, 2767-73).

The control level may be determined at the same time with the test biological sample by using a sample(s) previously collected and stored from a subject/subjects whose disease state (cancerous or non-cancerous) is/are known, as mentioned above. In a preferable embodiment of the present invention, the control level may be determined by using a sample(s) previously collected and stored from a subject/subjects whose disease state is/are prostate cancer with Gleason score 2-7 or a normal healthy subject/subjects. The immunostaining intensity of the STC2 polypeptide in a biological sample can be considered to be increased if it increases from the control level of the STC2 polypeptide by, for example, 10%, 25%, or 50%; or increases to more than 1.1 fold, more than 1.5 fold, more than 2.0 fold, more than 5.0 fold, more than 10.0 fold, or more.

I-2. Assessing Efficacy of Cancer Treatment

The STC2 gene differentially expressed between normal and PC cells also allow for the course of treatment of PC to be monitored, and the above-described method for diagnosing cancer can be applied for assessing the efficacy of a treatment on PC. Specifically, the efficacy of a treatment on PC can be assessed by determining the expression level of the STC2 gene in a cell(s) derived from a subject undergoing the treatment. If desired, test cell populations are obtained from the subject at various time points, before, during, and/or after the treatment. The expression level of the STC2 gene can be, for example, determined following the method described above under the item of 'I-1. Method for diagnosing cancer or a predisposition for developing cancer'. In the context of the present invention, it is preferred that the control level to which the detected expression level is compared is determined from the STC2 gene expression in a cell(s) not exposed to the treatment of interest.

If the expression level of the STC2 gene is compared to a normal control level, a similarity in the expression level indicates that the treatment of interest is efficacious and a difference in the expression level indicates less favorable clinical outcome or prognosis of that treatment. On the other hand, if the comparison is conducted against a cancerous control level, a difference in the expression level indicates efficacious treatment, while a similarity in the expression level indicates less favorable clinical outcome or prognosis.

Furthermore, the expression levels of the STC2 gene before and after a treatment can be compared according to the present method to assess the efficacy of the treatment. Specifically, the expression level detected in a subject-derived biological sample after a treatment (i.e., post-treatment level) is compared to the expression level detected in a biological sample obtained prior to treatment onset from the same subject (i.e., pre-treatment level). A decrease in the post-treatment level as compared to the pre-treatment level indicates that the treatment of interest is efficacious while an increase in or similarity of the post-treatment level to the pre-treatment level indicates less favorable clinical outcome or prognosis.

As used herein, the term "efficacious" indicates that the treatment leads to a reduction in the expression of a pathologically up-regulated gene, an increase in the expression of a pathologically down-regulated gene or a decrease in size, prevalence, or metastatic potential of carcinoma in a subject. When a treatment of interest is applied prophylactically, "efficacious" means that the treatment retards or prevents the forming of tumor or retards, prevents, or alleviates at least one clinical symptom of cancer. Assessment of the state of tumor in a subject can be made using standard clinical protocols. In addition, efficaciousness of a treatment can be determined in association with any known method for diagnosing cancer. Cancers can be diagnosed, for example, by identifying symptomatic anomalies, e.g., weight loss, abdominal pain, back pain, anorexia, nausea, vomiting and generalized malaise, weakness, and jaundice.

I-3. Assessing Prognosis of Subject with Cancer

The method for diagnosing PC described above can also be used for assessing the prognosis of PC in a subject. Thus, the present invention also provides a method for assessing the prognosis of a subject with PC. The expression level of the STC2 gene can be, for example, determined following the method described above under the item of 'I-1. Method for diagnosing cancer or a predisposition for developing cancer'. For example, the expression level of the STC2 gene in biological samples derived from patients over a spectrum of disease stages can be used as control levels to be compared with the expression level of the gene detected for a subject. By comparing the expression level of the STC2 gene in a subject and the control level(s) the prognosis of the subject can be assessed. Alternatively, by comparing over time the pattern of expression levels in a subject, the prognosis of the subject can be assessed.

For example, an increase in the expression level of STC2 gene in a subject as compared to a normal control level indicates less favorable prognosis. Conversely, a similarity in the expression level as compared to normal control level indicates a more favorable prognosis for the subject.

II. Kits:

The present invention also provides kits for detecting and/or diagnosing PC, which may also be useful in assessing the prognosis of cancer and/or monitoring the efficacy of a cancer therapy, i.e., kits that includes at least a reagent detecting the transcription or translation product of the STC2 gene. Examples of such reagents include nucleic acids that specifically bind to or identify a transcription product of the STC2 gene. For example, the nucleic acid that specifically bind to or identify a transcription product of the STC2 gene include such as oligonucleotides (e.g., probes and primers) having a sequence that is complementary to a portion of the STC2 gene transcription product. Alternatively, antibodies can be exemplified as reagents for detecting the translation product of the gene. The probes, primers, and antibodies described above under the item of 'I-1. Method for diagnosing cancer or a predisposition for developing cancer' can be mentioned as suitable examples of such reagents.

The translation product may also be detected based on its biological activity. The STC2 protein was reported to inhibit the phosphate uptake of a kidney cell line (Ishibashi K, et al., Biochem Biophys Res Commun 1998, Sep. 18; 250(2), 258-8). Thus, the inhibiting activity against the phosphate uptake of a kidney cell line may be detected for determining the expression level of the STC2 gene. For example, labeled phosphate, or other substrate(s) of the STC2 protein may be used as a reagent for detecting the expression level of the gene. Furthermore, according to the present invention, the translation product of STC2 gene has an ability to promote PC ell growth. Thus, according to an aspect of the present invention, a kit for detecting the expression of the STC2 gene may include a labeled phosphate and a kidney cell line, or a PC line and an appropriate medium.

The present kit is suited for detecting CRPC and aggressive PC with high Gleason score, in particular, Gleason score 8-10.

These reagents may be used for the above-described diagnosis of cancer. The assay format for using the reagents may be Northern hybridization or sandwich ELISA, both of which are well-known in the art.

The detection reagents may be packaged together in the form of a kit. For example, the detection reagents may be packaged in separate containers. Furthermore, the detection reagents may be packaged with other reagents necessary for the detection. For example a kit may include a nucleic acid or antibody (either bound to a solid matrix or packaged separately with reagents for binding them to the matrix) as the detection reagent, a control reagent (positive and/or negative), and/or a detectable label. Instructions (e.g., written, tape, VCR, CD-ROM, etc.) for carrying out the assay may also be included in the kit.

As an aspect of the present invention, the reagents for detecting cancer may be immobilized on a solid matrix, such as a porous strip, to form at least one site for detecting cancer. The measurement or detection region of the porous strip may include a plurality of sites, each containing a detection reagent (e.g., nucleic acid). A test strip may also contain sites for negative and/or positive controls. Alternatively, control sites may be located on a separate strip from the test strip. Optionally, the different detection sites may contain different amounts of immobilized detection reagents (e.g., nucleic acid), i.e., a higher amount in the first detection site and lesser amounts in subsequent sites. Upon the addition of test biological sample, the number of sites displaying a detectable signal provides a quantitative indication of the expression level of the STC2 gene in the sample. The detection sites may be configured in any suitably detectable shape and are typically in the shape of a bar or dot spanning the width of a test strip.

III. Screening Methods:

Using the STC2 gene, polypeptides encoded by the gene or fragments thereof, or transcriptional regulatory region(s) of the gene, it is possible to screen for candidate agents or substances that alter the expression of the gene or the biological activity of a polypeptide encoded by the gene. Such agents or substances can be used as pharmaceuticals for treating or preventing PC, in particular, CRPC and aggressive PC with high Gleason score (e.g., Gleason score 8-10). Thus, the present invention provides methods of screening for agents or substances for treating or preventing PC using the STC2 gene, polypeptide encoded by the gene or fragments thereof, or transcriptional regulatory region of the gene.

An agent or substance isolated by the screening method of the present invention is an agent or substance that is expected to inhibit the expression of the STC2 gene or the activity of the translation product of the gene, and thus, is a candidate for treating or preventing PC. The agents or substances are expected to be particularly suited for the treatment or prevention of CRPC and aggressive PC with high Gleason score (in particular, Gleason score 8-10). Namely, the agents or substances screened through the present methods are deemed to have a clinical benefit and can be further tested for its ability to prevent cancer cell growth in animal models or test subjects.

In the context of the present invention, agents or substances to be identified through the present screening methods may be any compound or composition including several compounds. Furthermore, the test agent or substance exposed to a cell or protein according to the screening methods of the present invention may be a single compound or a combination of compounds. When a combination of compounds is used in the methods, the compounds may be contacted sequentially or simultaneously.

Any test agent or substance, for example, cell extracts, cell culture supernatant, products of fermenting microorganism, extracts from marine organism, plant extracts, purified or crude proteins, peptides, non-peptide compounds, synthetic micromolecular compounds (including nucleic acid constructs, such as antisense RNA, siRNA, Ribozymes, etc.) and natural compounds can be used in the screening methods of the present invention. The test agent or substances of the present invention can be also obtained using any of the numerous approaches in combinatorial library methods known in the art, including (1) biological libraries,
(2) spatially addressable parallel solid phase or solution phase libraries,
(3) synthetic library methods requiring deconvolution,
(4) the "one-bead one-compound" library method and
(5) synthetic library methods using affinity chromatography selection.

The biological library methods using affinity chromatography selection is limited to peptide libraries, while the other four approaches are applicable to peptide, non-peptide oligomer or small molecule libraries of compounds (Lam, Anti-cancer Drug Des 1997, 12: 145-67). Examples of methods for the synthesis of molecular libraries can be found in the art (DeWitt et al., Proc Natl Acad Sci USA 1993, 90: 6909-13; Erb et al., Proc Natl Acad Sci USA 1994, 91: 11422-6; Zuckermann et al., J Med Chem 37: 2678-85, 1994; Cho et al., Science 1993, 261: 1303-5; Carell et al., Angew Chem Int Ed Engl 1994, 33: 2059; Carell et al., Angew Chem Int Ed Engl 1994, 33: 2061; Gallop et al., J Med Chem 1994, 37: 1233-51). Libraries of compounds may be presented in solution (see Houghten, Bio/Techniques 1992, 13: 412-21) or on beads (Lam, Nature 1991, 354: 82-4), chips (Fodor, Nature 1993, 364: 555-6), bacteria (U.S. Pat. No. 5,223,409), spores (U.S. Pat. Nos. 5,571,698, 5,403,484, and 5,223,409), plasmids (Cull et al., Proc Natl Acad Sci USA 1992, 89: 1865-9) or phage (Scott and Smith, Science 1990, 249: 386-90; Devlin, Science 1990, 249: 404-6; Cwirla et al., Proc Natl Acad Sci USA 1990, 87: 6378-82; Felici, J Mol Biol 1991, 222: 301-10; US Pat. Application 2002103360).

In another embodiment of the present invention, an agent or substance that binds to STC2 polypeptide and/or reduces the expression level of the STC2 gene may be used as a test agent or substance for the further screening for a candidate agent or substance that has the STC2 specific therapeutic effect.

A compound in which a part of the structure of the compound screened by any of the present screening methods is converted by addition, deletion and/or replacement, is included in the agents or substances obtained by the screening methods of the present invention.

Furthermore, when the screened test agent or substances is a protein, for obtaining a DNA encoding the protein, either the whole amino acid sequence of the protein may be determined to deduce the nucleic acid sequence coding for the protein, or partial amino acid sequence of the obtained protein may be analyzed to prepare an oligo DNA as a probe based on the sequence, and screen cDNA libraries with the probe to obtain a DNA encoding the protein. The obtained DNA find use in preparing the test agent or substance which is a candidate for treating or preventing cancer.

Test agents useful in the screenings described herein can also be antibodies that specifically bind to a STC2 protein or partial peptides thereof that lack the biological activity of the original proteins in vivo.

Although the construction of test agent libraries is well known in the art, herein below, additional guidance in identifying test agents and construction libraries of such agents for the present screening methods are provided.

(i) Molecular Modeling

Construction of test agent libraries is facilitated by knowledge of the molecular structure of compounds known to have the properties sought, and/or the molecular structure of STC2. One approach to preliminary screening of test agents suitable for further evaluation utilizes computer modeling of the interaction between the test agent and its target.

Computer modeling technology allows for the visualization of the three-dimensional atomic structure of a selected molecule and the rational design of new compounds that will interact with the molecule. The three-dimensional construct typically depends on data from x-ray crystallographic analysis or NMR imaging of the selected molecule. The molecular dynamics require force field data. The computer graphics systems enable prediction of how a new compound will link to the target molecule and allow experimental manipulation of the structures of the compound and target molecule to perfect binding specificity. Prediction of what the molecule-compound interaction will be when small changes are made in one or both requires molecular mechanics software and computationally intensive computers, usually coupled with user-friendly, menu-driven interfaces between the molecular design program and the user.

An example of the molecular modeling system described generally above includes the CHARMm and QUANTA programs, Polygen Corporation, Waltham, Mass. CHARMm performs the energy minimization and molecular dynamics functions. QUANTA performs the construction, graphic modeling and analysis of molecular structure. QUANTA allows interactive construction, modification, visualization, and analysis of the behavior of molecules with each other.

A number of articles have been published on the subject of computer modeling of drugs interactive with specific proteins, examples of which include Rotivinen et al. Acta Pharmaceutica Fennica 1988, 97: 159-66; Ripka, New Scientist 1988, 54-8; McKinlay & Rossmann, Annu Rev Pharmacol Toxiciol 1989, 29: 111-22; Perry & Davies, Prog Clin Biol Res 1989, 291: 189-93; Lewis & Dean, Proc R Soc Lond 1989, 236: 125-40, 141-62; and, with respect to a model receptor for nucleic acid components, Askew et al., J Am Chem Soc 1989, 111: 1082-90. Other computer programs that screen and graphically depict chemicals are available from companies such as BioDesign, Inc., Pasadena, Calif., Allelix, Inc, Mississauga, Ontario, Canada, and Hypercube, Inc., Cambridge, Ontario. See, e.g., DesJarlais et al., J Med Chem 1988, 31: 722-9; Meng et al., J Computer Chem 1992, 13: 505-24; Meng et al., Proteins 1993, 17: 266-78; Shoichet et al., Science 1993, 259: 1445-50.

Once a putative inhibitor has been identified, combinatorial chemistry techniques can be employed to construct any number of variants based on the chemical structure of the identified putative inhibitor, as detailed below. The resulting library of putative inhibitors, or "test agents" may be screened using the methods of the present invention to identify test agents suited to the treatment and/or prophylaxis of cancer and/or the prevention of post-operative recurrence of cancer, particularly wherein, such as prostate cancer.

(ii) Combinatorial Chemical Synthesis

Combinatorial libraries of test agents may be produced as part of a rational drug design program involving knowledge of core structures existing in known inhibitors. This approach allows the library to be maintained at a reasonable size, facilitating high throughput screening. Alternatively, simple, particularly short, polymeric molecular libraries may be constructed by simply synthesizing all permutations of the molecular family making up the library. An example of this latter approach would be a library of all peptides six amino acids in length. Such a peptide library could include every 6 amino acid sequence permutation. This type of library is termed a linear combinatorial chemical library.

Preparation of combinatorial chemical libraries is well known to those of skill in the art, and may be generated by either chemical or biological synthesis. Combinatorial chemical libraries include, but are not limited to, peptide libraries (see, e.g., U.S. Pat. No. 5,010,175; Furka, Int J Pept Prot Res 1991, 37: 487-93; Houghten et al., Nature 1991, 354: 84-6). Other chemistries for generating chemical diversity libraries can also be used. Such chemistries include, but are not limited to: peptides (e.g., PCT Publication No. WO 91/19735), encoded peptides (e.g., WO 93/20242), random bio-oligomers (e.g., WO 92/00091), benzodiazepines (e.g., U.S. Pat. No. 5,288,514), diversomers such as hydantoins, benzodiazepines and dipeptides (DeWitt et al., Proc Natl Acad Sci USA 1993, 90:6909-13), vinylogous polypeptides (Hagihara et al., J Amer Chem Soc 1992, 114: 6568), non-peptidal peptidomimetics with glucose scaffolding (Hirschmann et al., J Amer Chem Soc 1992, 114: 9217-8), analogous organic syntheses of small compound libraries (Chen et al., J. Amer Chem Soc 1994, 116: 2661), oligocarbamates (Cho et al., Science 1993, 261: 1303), and/or peptidylphosphonates (Campbell et al., J Org Chem 1994, 59: 658), nucleic acid libraries (see Ausubel, Current Protocols in Molecular Biology 1995 supplement; Sambrook et al., Molecular Cloning: A Laboratory Manual, 1989, Cold Spring Harbor Laboratory, New York, USA), peptide nucleic acid libraries (see, e.g., U.S. Pat. No. 5,539,083), antibody libraries (see, e.g., Vaughan et al., Nature Biotechnology 1996, 14(3):309-14 and PCT/US96/10287), carbohydrate libraries (see, e.g., Liang et al., Science 1996, 274: 1520-22; U.S. Pat. No. 5,593,853), and small organic molecule libraries (see, e.g., benzodiazepines, Gordon E M. Curr Opin Biotechnol. 1995 Dec. 1; 6(6):624-31; isoprenoids, U.S. Pat. No. 5,569, 588; thiazolidinones and metathiazanones, U.S. Pat. No. 5,549,974; pyrrolidines, U.S. Pat. Nos. 5,525,735 and 5,519, 134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Tripos, Inc., St. Louis, Mo., 3D Pharmaceuticals, Exton, Pa., Martek Biosciences, Columbia, Md., etc.).

(iii) Other Candidates

Another approach uses recombinant bacteriophage to produce libraries. Using the "phage method" (Scott & Smith, Science 1990, 249: 386-90; Cwirla et al., Proc Natl Acad Sci USA 1990, 87: 6378-82; Devlin et al., Science 1990, 249: 404-6), very large libraries can be constructed (e.g., $10^6$-$10^8$ chemical entities). A second approach uses primarily chemical methods, of which the Geysen method (Geysen et al., Molecular Immunology 1986, 23: 709-15; Geysen et al., J Immunologic Method 1987, 102: 259-74); and the method of Fodor et al. (Science 1991, 251: 767-73) are examples. Furka et al. (14th International Congress of Biochemistry 1988, Volume #5, Abstract FR:013; Furka, Int J Peptide Protein Res 1991, 37: 487-93), Houghten (U.S. Pat. No. 4,631,211) and Rutter et al. (U.S. Pat. No. 5,010,175) describe methods to produce a mixture of peptides that can be tested as agonists or antagonists. Aptamers are macromolecules composed of nucleic acid that bind tightly to a specific molecular target. Tuerk and Gold (Science. 249:505-510 (1990)) discloses SELEX (Systematic Evolution of Ligands by Exponential Enrichment) method for selection of aptamers. In the SELEX method, a large library of nucleic acid molecules (e.g., $10^{15}$ different molecules) can be used for screening.

III. Screening Methods for Anti Cancer Compound

According to the present invention, the expression of the STC2 gene was suggested to be crucial for the growth and/or survival of cancer cells, in particular PC cells, more particularly CRPC cells and aggressive PC cells with high Gleason score (e.g., Gleason score 8-10). Therefore, it was considered that agents or substances that suppress the function of the polypeptide encoded by the STC2 gene would reduce or inhibit the growth and/or survival of cancer cells, and thus find use in the treatment and prevention of prostate cancer. Accordingly, the present invention provides methods of screening an agent for treating or preventing cancer, using the STC2 polypeptide.

In addition to the STC2 polypeptide, fragments of the polypeptide may be used for the present screening so long as it retains at least one biological activity of the natural occurring STC2 polypeptide.

The polypeptide or fragments thereof may be further linked to other substances so long as the polypeptide and fragments retains at least one of its biological activity. Usable substances include: peptides, lipids, sugar and sugar chains, acetyl groups, natural and synthetic polymers, etc. These kinds of modifications may be performed to confer additional functions or to stabilize the polypeptide and fragments.

The polypeptide or fragments used for the present method may be obtained from nature as naturally occurring proteins via conventional purification methods or through chemical synthesis based on the selected amino acid sequence. For example, conventional peptide synthesis methods that can be adopted for the synthesis include:

1) Peptide Synthesis, Interscience, New York, 1966;
2) The Proteins, Vol. 2, Academic Press, New York, 1976;
3) Peptide Synthesis (in Japanese), Maruzen Co., 1975;
4) Basics and Experiment of Peptide Synthesis (in Japanese), Maruzen Co., 1985;
5) Development of Pharmaceuticals (second volume) (in Japanese), Vol. 14 (peptide synthesis), Hirokawa, 1991;
6) WO99/67288; and
7) Barany G. & Merrifield R. B., Peptides Vol. 2, "Solid Phase Peptide Synthesis", Academic Press, New York, 1980, 100-118.

Alternatively, the protein may be obtained adopting any known genetic engineering methods for producing polypeptides (e.g., Morrison J., J Bacteriology 1977, 132: 349-51; Clark-Curtiss & Curtiss, Methods in Enzymology (eds. Wu et al.) 1983, 101: 347-62). For example, first, a suitable vector including a polynucleotide encoding the objective protein in an expressible form (e.g., downstream of a promoter regulatory sequence) is prepared, transformed into a suitable host cell, and then the host cell is cultured to produce the protein. More specifically, a gene encoding the STC2 polypeptide is expressed in host (e.g., animal) cells and such by inserting the gene into a vector for expressing foreign genes, such as pSV2neo, pcDNA I, pcDNA3.1, pCAGGS, or pCD8. A promoter may be used for the expression. Any commonly used promoters may be employed including, for example, the SV40 early promoter (Rigby in Williamson (ed.), Genetic Engineering, vol. 3. Academic Press, London, 1982, 83-141), the EF-alpha promoter (Kim et al., Gene 1990, 91:217-23), the CAG promoter (Niwa et al., Gene 1991, 108:193), the RSV LTR promoter (Cullen, Methods in Enzymology 1987, 152:684-704), the SR alpha promoter (Takebe et al., Mol Cell Biol 1988, 8:466), the CMV immediate early promoter (Seed et al., Proc Natl Acad Sci USA 1987, 84:3365-9), the SV40 late promoter (Gheysen et al., J Mol Appl Genet. 1982, 1:385-94), the Adenovirus late promoter (Kaufman et al., Mol Cell Biol 1989, 9:946), the HSV TK promoter, and such. The introduction of the vector into host cells to express the STC2 gene can be performed according to any methods, for example, the electroporation method (Chu et al., Nucleic Acids Res 1987, 15:1311-26), the calcium phosphate method (Chen et al., Mol Cell Biol 1987, 7:2745-52), the DEAE dextran method (Lopata et al., Nucleic Acids Res 1984, 12:5707-17; Sussman et al., Mol Cell Biol 1985, 4:1641-3), the Lipofectin method (Derijard B, Cell 1994, 7:1025-37; Lamb et al., Nature Genetics 1993, 5:22-30; Rabindran et al., Science 1993, 259:230-4), and such.

The STC2 protein may also be produced in vitro adopting an in vitro translation system.

The STC2 polypeptide to be contacted with a test agent or substance can be, for example, a purified polypeptide, a soluble protein, or a fusion protein fused with other polypeptides.

Any test agent or substance, for example, cell extracts, cell culture supernatant, products of fermenting microorganism, extracts from marine organism, plant extracts, purified or crude proteins, peptides, non-peptide compounds, synthetic micromolecular compounds (including nucleic acid constructs, such as antisense RNA, siRNA, Ribozymes, and aptamer etc.) and natural compounds can be used in the screening methods of the present invention. The test agent or substance of the present invention can be also obtained using any of the numerous approaches in combinatorial library methods known in the art, including (1) biological libraries, (2) spatially addressable parallel solid phase or solution phase libraries, (3) synthetic library methods requiring deconvolution, (4) the "one-bead one-compound" library method and (5) synthetic library methods using affinity chromatography selection. The biological library methods using affinity chromatography selection is limited to peptide libraries, while the other four approaches are applicable to peptide, non-peptide oligomer or small molecule libraries of compounds (Lam, Anticancer Drug Des 1997, 12: 145-67). Examples of methods for the synthesis of molecular libraries can be found in the art (DeWitt et al., Proc Natl Acad Sci USA 1993, 90: 6909-13; Erb et al., Proc Natl Acad Sci USA 1994, 91: 11422-6; Zuckermann et al., J Med Chem 37: 2678-85, 1994; Cho et al., Science 1993, 261: 1303-5; Carell et al., Angew Chem Int Ed Engl 1994, 33: 2059; Carell et al., Angew Chem Int Ed Engl 1994, 33: 2061; Gallop et al., J Med Chem 1994, 37: 1233-51). Libraries of compounds may be presented in solution (see Houghten, Bio/Techniques 1992, 13: 412-21) or on beads (Lam, Nature 1991, 354: 82-4), chips (Fodor, Nature 1993, 364: 555-6), bacteria (U.S. Pat. No. 5,223,409), spores (U.S. Pat. Nos. 5,571,698; 5,403,484, and 5,223,409), plasmids (Cull et al., Proc Natl Acad Sci USA 1992, 89: 1865-9) or phage (Scott and Smith, Science 1990, 249: 386-90; Devlin, Science 1990, 249: 404-6; Cwirla et al., Proc Natl Acad Sci USA 1990, 87: 6378-82; Felici, J Mol Biol 1991, 222: 301-10; US Pat. Application 2002103360).

A compound in which a part of the structure of the compound screened by any of the present screening methods is converted by addition, deletion and/or replacement, is included in the agents or substances obtained by the screening methods of the present invention.

Furthermore, when the screened test agent or substance is a protein, for obtaining a DNA encoding the protein, either the whole amino acid sequence of the protein may be determined to deduce the nucleic acid sequence coding for the protein, or partial amino acid sequence of the obtained protein may be analyzed to prepare an oligo DNA as a probe based on the sequence, and screen cDNA libraries with the probe to obtain a DNA encoding the protein. The obtained DNA is confirmed it's usefulness in preparing the test agent which is a candidate for treating or preventing cancer.

III-1. Identifying Agents or Substances that Bind to STC2 Polypeptide

An agent or substance that binds to a protein is likely to alter the expression of the gene coding for the protein or the biological activity of the protein. Thus, as an aspect, the present invention provides a method of screening an agent for treating or preventing cancer, that includes the steps of:
a) contacting a test agent or substance with the STC2 polypeptide or a fragment thereof;
b) detecting the binding between the polypeptide or fragment and the test agent or substance; and
c) selecting the test agent or substance that binds to the polypeptide as a candidate agent for treating or preventing cancer.

According to the present invention, the therapeutic effect of the test agent or substance on inhibiting the cell growth or a candidate agent or substance for treating or preventing STC2 associating cancer may be evaluated. Therefore, the present invention also provides a method of screening for a candidate agent or substance for inhibiting the cell growth or a candidate agent or substance for treating or preventing STC2 associating cancer, using the STC2 polypeptide or fragments thereof including the steps as follows:
a) contacting a test agent or substance with the STC2 polypeptide or a functional fragment thereof; and
b) detecting the binding level between the polypeptide or functional fragment and the test agent or substance of step (a), and
c) correlating the binding level of b) with the therapeutic effect of the test agent or substance.

In the present invention, the therapeutic effect may be correlated with the binding level of STC2 polypeptide or a functional fragment thereof. For example, when the test agent or substance bind to STC2 polypeptide or a functional fragment thereof, the test agent or substance may identified or selected as the candidate agent or substance having the therapeutic effect. Alternatively, when the test agent or substance does not bind to STC2 polypeptide or a functional fragment thereof, the test agent or substance may identified as the agent or substance having no significant therapeutic effect.

The binding of a test agent or substance to the STC2 polypeptide may be, for example, detected by immunoprecipitation using an antibody against the polypeptide. Therefore, for the purpose for such detection, it is preferred that the STC2 polypeptide or fragments thereof used for the screening contains an antibody recognition site. The antibody used for the screening may be one that recognizes an antigenic region (e.g., epitope) of the present STC2 polypeptide which preparation methods are well known in the art, and any method may be employed in the present invention to prepare such antibodies and equivalents thereof.

Alternatively, the STC2 polypeptide or a fragment thereof may be expressed as a fusion protein having at its N- or C-terminus a recognition site (epitope) of a monoclonal antibody, whose specificity has been revealed, to the N- or C-terminus of the polypeptide. A commercially available epitope-antibody system can be used (Experimental Medicine 1995, 13:85-90). Vectors which can express a fusion protein with, for example, beta-galactosidase, maltose binding protein, glutathione S-transferase, green florescence protein (GFP), and such by the use of its multiple cloning sites are commercially available and can be used for the present invention. Furthermore, fusion proteins containing much smaller epitopes to be detected by immuno-precipitation with an antibody against the epitopes are also known in the art (Experimental Medicine 1995, 13:85-90). Such epitopes, composed of several to a dozen amino acids so as not to change the property of the STC2 polypeptide or fragments thereof, can also be used in the present invention. Examples include polyhistidine (His-tag), influenza aggregate HA, human c-myc, FLAG, Vesicular stomatitis virus glycoprotein (VSV-GP), T7 gene 10 protein (T7-tag), human simple herpes virus glycoprotein (HSV-tag), E-tag (an epitope on monoclonal phage), and such.

Glutathione S-transferase (GST) is also well-known as the counterpart of the fusion protein to be detected by immuno-precipitation. When GST is used as the protein to be fused with the STC2 polypeptide or fragment thereof to form a fusion protein, the fusion protein can be detected either with an antibody against GST or a substance specifically binding to GST, i.e., such as glutathione (e.g., glutathione-Sepharose 4B).

In immunoprecipitation, an immune complex is formed by adding an antibody (recognizing the STC2 polypeptide or a fragment thereof itself, or an epitope tagged to the polypeptide or fragment) to the reaction mixture of the STC2 polypeptide and the test agent or substances. If the test agent or substance has the ability to bind the polypeptide, then the formed immune complex will include the STC2 polypeptide, the test agent or substance, and the antibody. On the contrary, if the test agent or substance are devoid of such ability, then the formed immune complex only include the STC2 polypeptide and the antibody. Therefore, the binding ability of a test agent or substance to STC2 polypeptide can be examined by, for example, measuring the size of the formed immune complex. Any method for detecting the size of a substance can be used, including chromatography, electrophoresis, and such. For example, when mouse IgG antibody is used for the detection, Protein A or Protein G sepharose can be used for quantitating the formed immune complex.

Immunoprecipitation can be performed by following or according to, for example, the methods in the literature (See, for example, Harlow et al., Antibodies, Cold Spring Harbor Laboratory publications, New York, 1988, 511-52).

Furthermore, the STC2 polypeptide or a fragment thereof used for the screening of agent or substance that bind to thereto may be bound to a carrier. Example of carriers that may be used for binding the polypeptides include insoluble polysaccharides, such as agarose, cellulose and dextran; and synthetic resins, such as polyacrylamide, polystyrene and silicon; preferably commercially available beads and plates (e.g., multi-well plates, biosensor chip, etc.) prepared from the above materials may be used. When using beads, they may be filled into a column. Alternatively, the use of magnetic beads is also known in the art, and enables to readily isolate polypeptides and agents or substances bound on the beads via magnetism.

The binding of a polypeptide to a carrier may be conducted according to routine methods, such as chemical bonding and physical adsorption. Alternatively, a polypeptide may be bound to a carrier via antibodies specifically recognizing the protein. Moreover, binding of a polypeptide to a carrier can also be conducted by means of interacting molecules, such as the combination of avidin and biotin.

Screening using such carrier-bound STC2 polypeptide or fragments thereof include, for example, contacting a test agent or substance to the carrier-bound polypeptide, incubating the mixture, washing the carrier, and detecting and/or measuring the agent or substance bound to the carrier. The binding may be carried out in buffer, for example, but are not limited to, phosphate buffer and Tris buffer, as long as the buffer does not inhibit the binding.

A screening method wherein such carrier-bound STC2 polypeptide or fragments thereof and a composition (e.g., cell extracts, cell lysates, etc.) are used as the test agent or substance, such method is generally called affinity chromatography. For example, the STC2 polypeptide may be immobilized on a carrier of an affinity column, and a test agent or substance, containing a substance capable of binding to the polypeptides, is applied to the column. After loading the test agent or substance, the column is washed, and then the substance bound to the polypeptide is eluted with an appropriate buffer.

A biosensor using the surface plasmon resonance phenomenon may be used as a mean for detecting or quantifying the bound agent or substance in the present invention. When such a biosensor is used, the interaction between the STC2 polypeptide and a test agent or substance can be observed real-time as a surface plasmon resonance signal, using only a minute amount of the polypeptide and without labeling (for example, BIAcore, Pharmacia). Therefore, it is possible to evaluate the binding between the polypeptide and test agent or substance using a biosensor such as BIAcore.

Methods of screening for molecules that bind to a specific protein among synthetic chemical compounds, or molecules in natural substance banks or a random phage peptide display library by exposing the specific protein immobilized on a carrier to the molecules, and methods of high-throughput screening based on combinatorial chemistry techniques (Wrighton et al., Science 1996, 273:458-64; Verdine, Nature 1996, 384:11-3) to isolate not only proteins but chemical compounds are also well-known to those skilled in the art. These methods can also be used for screening agents or substances (including agonist and antagonist) that bind to the STC2 protein or fragments thereof.

When the test agent or substance is a protein, for example, West-Western blotting analysis (Skolnik et al., Cell 1991, 65:83-90) can be used for the present method. Specifically, a protein binding to the STC2 polypeptide can be obtained by preparing first a cDNA library from cells, tissues, organs, or cultured cells (e.g., PC cell lines) expected to express at least one protein binding to the STC2 polypeptide using a phage vector (e.g., ZAP), expressing the proteins encoded by the vectors of the cDNA library on LB-agarose, fixing the expressed proteins on a filter, reacting the purified and labeled STC2 polypeptide with the above filter, and detecting the plaques expressing proteins to which the STC2 polypeptide has bound according to the label of the STC2 polypeptide.

Labeling substances such as radioisotope (e.g., $^{3}H$, $^{14}C$, $^{32}P$, $^{33}P$, $^{35}S$, $^{125}I$, $^{131}I$), enzymes (e.g., alkaline phosphatase, horseradish peroxidase, beta-galactosidase, beta-glucosidase), fluorescent substances (e.g., fluorescein isothiocyanate (FITC), rhodamine) and biotin/avidin, may be used for the labeling of STC2 polypeptide in the present method. When the protein is labeled with radioisotope, the detection or measurement can be carried out by liquid scintillation. Alternatively, when the protein is labeled with an enzyme, it can be detected or measured by adding a substrate of the enzyme to detect the enzymatic change of the substrate, such as generation of color, with absorptiometer. Further, in case where a fluorescent substance is used as the label, the bound protein may be detected or measured using fluorophotometer.

Moreover, the STC2 polypeptide bound to the protein can be detected or measured by utilizing an antibody that specifically binds to the STC2 polypeptide, or a peptide or polypeptide (for example, GST) that is fused to the STC2 polypeptide. In case of using an antibody in the present screening, the antibody is preferably labeled with one of the labeling substances mentioned above, and detected or measured based on the labeling substance. Alternatively, the antibody against the STC2 polypeptide may be used as a primary antibody to be detected with a secondary antibody that is labeled with a labeling substance. Furthermore, the antibody bound to the STC2 polypeptide in the present screening may be detected or measured using protein G or protein A column. Alternatively, in another embodiment of the screening method of the present invention, two-hybrid system utilizing cells may be used ("MATCHMAKER Two-Hybrid system", "Mammalian MATCHMAKER Two-Hybrid Assay Kit", "MATCHMAKER one-Hybrid system" (Clontech); "HybriZAP Two-Hybrid Vector System" (Stratagene); the references "Dalton et al., Cell 1992, 68:597-612" and "Fields et al., Trends Genet. 1994, 10:286-92"). In two-hybrid system, STC2 polypeptide or a fragment thereof is fused to the SRF-binding region or GAL4-binding region and expressed in yeast cells. A cDNA library is prepared from cells expected to express at least one protein binding to the STC2 polypeptide, such that the library, when expressed, is fused to the VP16 or GAL4 transcriptional activation region. The cDNA library is then introduced into the above yeast cells and the cDNA derived from the library is isolated from the positive clones detected (when a protein binding to the STC2 polypeptide is expressed in the yeast cells, the binding of the two activates a reporter gene, making positive clones detectable). A protein encoded by the cDNA can be prepared by introducing the cDNA isolated above to E. coli and expressing the protein.

As a reporter gene, for example, Ade2 gene, lacZ gene, CAT gene, luciferase gene and such can be used in addition to the HIS3 gene.

The agent or substance isolated by this screening is a candidate for antagonists of the STC2 polypeptide. The term "antagonist" refers to molecules that inhibit the function of the polypeptide by binding thereto.

In the present invention, it is revealed that suppressing the expression of STC2, reduces prostate cancer cell growth. Thus, by screening for candidate agents or compounds that bind to polypeptide, candidate compounds that find use to treat or prevent Prostate cancers can be identified. The potential of these candidate substance or compounds to treat or prevent prostate cancers may be evaluated by a secondary and/or further screening to identify therapeutic agents useful in treating or preventing prostate cancers. For example, when a compound binding to STC2 protein inhibits, e.g., the proliferative activity or activity to inhibit phosphate uptake of prostate cancer cells, it may be concluded that such compound has the STC2 specific therapeutic effect.

III-2. Identifying Agents or Substances by Detecting Biological Activity of the STC2 Polypeptide According to the present invention, the expression of STC2 gene was shown to be crucial for the growth and/or survival of cancer cells, in particular, prostate cancer cells, more particularly, CRPC cells and aggressive PC cells with high Gleason score (e.g., Gleason score 8-10). Therefore, agents or substances that suppress or inhibit the biological function of the translational product of the STC2 gene is considered to serve as candidates for treating or preventing cancer. Thus, the present invention also provides a method for screening a compound for treating or preventing cancer using the STC2 polypeptide or fragments thereof including the steps as follows:

a) contacting a test agent or substance with the STC2 polypeptide or a fragment thereof; and b) detecting the biological activity of the polypeptide or fragment of step (a).

Any polypeptide can be used for the screening so long as it has a biological activity equivalent to the STC2 polypeptide that can be used as an index in the present screening method. According to the present invention, the STC2 polypeptide has been demonstrated to be required for the growth or viability of PC cells (more specifically, CRPC cells and aggressive PC with high Grealon score). Furthermore, the STC2 was reported to inhibit the phosphate uptake of kidney cell line. Therefore, biological activities of the STC2 polypeptide that can be used as an index for the screening include such cell growth promoting activity and the inhibiting activity against phosphate uptake of a kidney cell line. For example, a human STC2 polypeptide can be used and polypeptides functionally equivalent thereto including fragments thereof can also be used. Such polypeptides may be expressed endogenously or exogenously by suitable cells.

When the biological activity to be detected in the present method is cell proliferation, detection may be accomplished, for example, by preparing cells which express the STC2 polypeptide or a fragment thereof (e.g., 22Rv1, LNCaP, C4-2B, DU145, PC-3, etc.), culturing the cells in the presence of a test agent or substance, and determining the speed of cell proliferation, measuring the cell cycle and such, as well as by detecting wound-healing activity, conducting Matrigel invasion assay and measuring the colony forming activity.

According to an aspect of the present invention, the screening further includes, after the above step (b), the steps of:

c) comparing the biological activity of the polypeptide or fragment with the biological activity detected in the absence of the agent or substance; and d) selecting the agent or substance that suppresses the biological activity of the polypeptide as a candidate agent for treating or preventing PC.

According to the present invention, the therapeutic effect of the test agent or substance on inhibiting the cell growth or a candidate agent or substance for treating or preventing STC2 associating cancer may be evaluated. Therefore, the present invention also provides a method of screening for a candidate agent or substance for inhibiting the cell growth or a candidate agent or substance for treating or preventing STC2 associating cancer, using the STC2 polypeptide or fragments thereof including the steps as follows:

a) contacting a test agent or substance with the STC2 polypeptide or a functional fragment thereof; and b) detecting the biological activity of the polypeptide or fragment of step (a), and c) correlating the biological activity of b) with the therapeutic effect of the test agent or substance.

In the present invention, the therapeutic effect may be correlated with the biological activity STC2 polypeptide or a functional fragment thereof. For example, when the test agent or substance suppresses or inhibits the biological activity of STC2 polypeptide or a functional fragment thereof as compared to a level detected in the absence of the test agent or substance, the test agent or substance may identified or selected as the candidate agent or substance having the therapeutic effect. Alternatively, when the test agent or substance does not suppress or inhibit the biological activity of STC2 polypeptide or a functional fragment thereof as compared to a level detected in the absence of the test agent or substance, the test agent or substance may be identified as the agent or compound having no significant therapeutic effect.

In the preferred embodiments, control cells which do not express STC2 polypeptide are used. Accordingly, the present invention also provides a method of screening for a candidate substance for inhibiting the cell growth or a candidate substance for treating or preventing STC2 associating disease, using the STC2 polypeptide or fragments thereof including the steps as follows:

a) culturing cells which express a STC2 polypeptide or a functional fragment thereof, and control cells that do not express a STC2 polypeptide or a functional fragment thereof in the presence of the test substance;

b) detecting the biological activity of the cells which express the protein and control cells; and c) selecting the test compound that inhibits the biological activity in the cells which express the protein as compared to the proliferation detected in the control cells and in the absence of said test substance.

Moreover, the present invention also provides a screening method following the method described in III-1, including the steps of:

a) contacting a test agent or substance with the STC2 polypeptide or a fragment thereof;

b) detecting the binding between the polypeptide or fragment and the test agent or substance;

c) selecting the test agent or substance that binds to the polypeptide;

d) contacting the test agent or substance selected in step c) with the STC2 polypeptide or a fragment thereof;

e) comparing the biological activity of the polypeptide or fragment with the biological activity detected in the absence of the agent or substance; and f) selecting the agent or substance that suppresses the biological activity of the polypeptide as a candidate agent for treating or preventing PC.

The agent or substance isolated by this screening is a candidate for an antagonist of the STC2 polypeptide, and thus, is a candidate that inhibits the in vivo interaction of the polypeptide with molecules (including nucleic acids (RNAs and DNAs) and proteins). In the present invention, the STC2 gene plays the crucial role in the cell proliferation showing in the example 4 and 5. Therefore, a biological activity of STC2 to be detected in the present screening method may be its cell proliferation activity.

Moreover, STC2 polypeptide was reported to inhibit the phosphate uptake of a kidney cell line. Accordingly, a phosphate uptake activity in a kidney cell line may also be detected as a biological activity of STC2. Therefore, the present invention further provides a method for screening an agent for treating or preventing cancer. An embodiment of this screening method includes the steps of:

(a) contacting a cell that expresses the STC2 polypeptide or a fragment thereof with an agent or substance;

(b) detecting the inhibiting activity of the STC2 polypeptide against the phosphate uptake of a kidney cell line;

(c) comparing the inhibiting activity of the STC2 polypeptide against the phosphate uptake detected in the absence of the agent or substance; and (d) selecting the agent or substance that suppresses the inhibiting activity of the STC2 polypeptide against the phosphate uptake activity as a candidate agent or substance for treating or preventing cancer.

According to this screening method, candidate compounds for suppressing the growth of PC cells, especially CRPC and aggressive PC with high Gleason score (e.g., Gleason score 8-10), can be identified.

III-3. Identifying Agents or Substances by Detecting Expression Level of the STC2 Gene in a Cell As discussed in detail above, by controlling the expression level of the STC2 gene, one can control the onset and progression of PC. Thus, agents or substances that may be used in the treatment or prevention of PCs, in particular, CRPC and aggressive PC with high Gleason score (e.g., Gleason score 8-10) can be identified through screenings that use the expression levels of STC2 gene as indices. In the context of the present invention, such screening may include, for example, the following steps:

a) contacting a test agent or substance with a cell expressing the STC2 gene;
b) detecting the expression level of the STC2 gene;
c) comparing the expression level with the expression level detected in the absence of the agent or substance; and
d) selecting the agent or substance that reduces the expression level as a candidate agent for treating or preventing cancer.

According to the present invention, the therapeutic effect of the test agent or substance on inhibiting the cell growth or a candidate agent or substance for treating or preventing STC2 associating cancer may be evaluated. Therefore, the present invention also provides a method for screening a candidate agent or substance that suppresses the proliferation of cancer cells, and a method for screening a candidate agent or substance for treating or preventing STC2 associating cancer.

In the context of the present invention, such screening may include, for example, the following steps:
a) contacting a test agent or substance with a cell expressing the STC2 gene;
b) detecting the expression level of the STC2 gene; and
c) correlating the expression level of b) with the therapeutic effect of the test agent or substance.

In the context of the present invention, the therapeutic effect may be correlated with the expression level of the STC2 gene. For example, when the test agent or substance reduces the expression level of the STC2 gene as compared to a level detected in the absence of the test agent or substance, the test agent or substance may identified or selected as the candidate agent or substance having the therapeutic effect. Alternatively, when the test agent or substance does not reduce the expression level of the STC2 gene as compared to a level detected in the absence of the test agent or substance, the test agent or substance may be identified as the agent or substance having no significant therapeutic effect.

An agent or substance that inhibits the expression of the STC2 gene or the activity of its gene product can be identified by contacting a cell expressing the STC2 gene with a test agent or substance and then determining the expression level of the STC2 gene. Naturally, the identification may also be performed using a population of cells that express the gene in place of a single cell. A decreased expression level detected in the presence of an agent or substance as compared to the expression level in the absence of the agent or substance indicates the agent as being an inhibitor of the STC2 gene, suggesting the possibility that the agent is useful for inhibiting PC, thus a candidate agent to be used for the treatment or prevention of PC, in particular, CRPC and aggressive PC (e.g., Gleason score 8-10).

The expression level of a gene can be estimated by methods well known to one skilled in the art. The expression level of the STC2 gene can be, for example, determined following the method described above under the item of 'I-1. Method for diagnosing cancer or a predisposition for developing cancer'. The cell or the cell population used for such identification may be any cell or any population of cells so long as it expresses the STC2 gene. For example, the cell or population may be or contain an immortalized cell derived from a carcinoma cell, including PC cell. Cells expressing the STC2 gene include, for example, cell lines established from cancers (e.g., PC cell lines such as 22Rv1, LNCaP, C4-2B, DU145, PC-3, etc.). Furthermore, the cell or population may be or contain a cell which has been transfected with the STC2 gene.

The present method allows screening of various agents or substances mentioned above and is particularly suited for screening functional nucleic acid molecules including antisense RNA, siRNA, and such.

III-4. Identifying Agents or Substances Using Transcriptional Regulatory Region of STC2 Gene According to another aspect, the present invention provides a method which includes the following steps of:

a) contacting a test agent or substance with a cell into which a vector, including the transcriptional regulatory region of the STC2 gene and a reporter gene that is expressed under the control of the transcriptional regulatory region, has been introduced;
b) detecting the expression or activity of said reporter gene;
c) comparing the expression level or activity with the expression level or activity detected in the absence of the agent or substance; and
d) selecting the agent or substance that reduces the expression or activity of said reporter gene as a candidate agent for treating or preventing cancer.

According to the present invention, the therapeutic effect of the test agent or substance on inhibiting the cell growth or a candidate agent or substance for treating or preventing STC2 associating cancer may be evaluated. Therefore, the present invention also provides a method for screening a candidate agent or substance that suppresses the proliferation of cancer cells, and a method for screening a candidate agent or compound for treating or preventing STC2 associating cancer.

According to another aspect, the present invention provides a method which includes the following steps of:

a) contacting a test agent or substance with a cell into which a vector, composed of the transcriptional regulatory region of the STC2 gene and a reporter gene that is expressed under the control of the transcriptional regulatory region, has been introduced;
b) detecting the expression level or activity of said reporter gene; and
c) correlating the expression level of b) with the therapeutic effect of the test agent or substance.

In the context of the present invention, the therapeutic effect may be correlated with the expression level or activity of said reporter gene. For example, when the test agent or substance reduces the expression level or activity of said reporter gene as compared to a level detected in the absence of the test agent or substance, the test agent or substance may be identified or selected as the candidate agent or substance having the therapeutic effect. Alternatively, when the test agent or substance does not reduce the expression level or activity of said reporter gene as compared to a level detected in the absence of the test agent or substance, the test agent or substance may be identified as the agent or substance having no significant therapeutic effect.

Suitable reporter genes and host cells are well known in the art. For example, reporter genes are luciferase, green florescence protein (GFP), *Discosoma* sp. Red Fluorescent Protein (DsRed), Chrolamphenicol Acetyltransferase (CAT), lacZ and betaglucuronidase (GUS), and host cell is COS7, HEK293, HeLa and so on. The reporter construct required for the screening can be prepared by connecting reporter gene sequence to the transcriptional regulatory region of STC2. The transcriptional regulatory region of STC2 herein is the region from start codon to at least 500 bp upstream, preferably 1000 bp, more preferably 5000 or 10000 bp upstream. A nucleotide segment containing the transcriptional regulatory region can be isolated from a genome library or can be propagated by PCR. The reporter construct required for the screening can be prepared by connecting reporter gene sequence to the transcriptional regulatory region of any one of these genes. Methods for identifying a transcriptional regulatory region, and also assay protocol are well known (Molecular Cloning third edition chapter 17, 2001, Cold Springs Harbor Laboratory Press).

The vector containing the said reporter construct is infected to host cells and the expression or activity of the reporter gene is detected by method well known in the art (e.g., using luminometer, absorption spectrometer, flow cytometer and so on). "reduces the expression or activity" as defined herein are preferably at least 10% reduction of the expression or activity of the reporter gene in comparison with in absence of the compound, more preferably at least 25%, 50% or 75% reduction and most preferably at 95% reduction.

III-5. Selecting Therapeutic Agents or Substances that are Appropriate for a Particular Individual Differences in the genetic makeup of individuals can result in differences in their relative abilities to metabolize various drugs. An agent or substance that is metabolized in a subject to act as an anti-tumor agent or substance can manifest itself by inducing a change in a gene expression pattern in the subject's cells from that characteristic of a cancerous state to a gene expression pattern characteristic of a non cancerous state. Accordingly, the STC2 gene differentially expressed between non-cancerous prostate cells and cancerous prostate cells, in particular, CRPC cells and aggressive PC cells (e.g., Gleason score 8-10), disclosed herein allow for a putative therapeutic or prophylactic inhibitor of PC (in particular, CRPC and aggressive PC) to be tested in a test cell population from a selected subject in order to determine if the agent or substance are a suitable inhibitor of PC in the subject.

To identify an inhibitor of PC that is appropriate for a specific subject, a test cell population from the subject is exposed to a candidate therapeutic agent or substance, and the expression of STC2 gene is determined.

In the context of the method of the present invention, test cell populations contain cells expressing the STC2 gene. Preferably, the test cell is a PC cell, more preferably, a CRPC cell or an aggressive PC cell (e.g., Gleason score 8-10).

Specifically, a test cell population may be incubated in the presence of a candidate therapeutic agent or substance and the expression of the STC2 gene in the test cell population may be measured and compared to one or more reference profiles, e.g., a cancerous reference expression profile or a non-cancerous reference expression profile. A decrease in the expression of the STC2 gene in a test cell population relative to a reference cell population containing cancerous cells indicates that the agent or substance have therapeutic potential. Alternatively, a similarity in the expression of the STC2 gene in a test cell population relative to a reference cell population not containing cancerous cells indicates that the agent or substance have therapeutic potential.

IV. Double-Stranded Molecules and Use Thereof.

IV-1. Double-Stranded Molecules

Double-stranded molecules targeting the STC2 gene can inhibit the expression of the STC2 gene and cell proliferation when the molecule introduced into a cell expressing the STC2 gene (Example 4). Accordingly, present invention provides for such double-stranded molecules and methods of use the same to target the STC2 gene.

The term "isolated double-stranded molecule" refers to a nucleic acid molecule that inhibits expression of a target gene including, for example, short interfering RNA (siRNA; e.g., double-stranded ribonucleic acid (dsRNA) or small hairpin RNA (shRNA)) and short interfering DNA/RNA (siD/R-NA; e.g. double-stranded chimera of DNA and RNA (dsD/R-NA) or small hairpin chimera of DNA and RNA (shD/R-NA)).

As used herein, sense strand of a target sequence is a nucleotide sequence within mRNA or cDNA sequence of a gene, which will result in suppress of translation of the whole mRNA if a double-stranded nucleic acid molecule of the present invention was introduced within a cell expressing the gene. A nucleotide sequence within mRNA or cDNA sequence of a gene can be determined to be a target sequence when a double-stranded polynucleotide including a sequence corresponding to the target sequence inhibits expression of the gene in a cell expressing the gene. The double stranded polynucleotide by which suppresses the gene expression may be composed of the target sequence and 3' overhang (e.g., uu).

As used herein, the term "siRNA" refers to a double-stranded RNA molecule which prevents translation of a target mRNA. Standard techniques of introducing siRNA into the cell are used, including those in which DNA is a template from which RNA is transcribed. The siRNA includes a sense nucleic acid sequence (also referred to as "sense strand") of the STC2 gene, a antisense nucleic acid sequence (also referred to as "antisense strand") of the STC2 gene or both. The siRNA may be constructed such that a single transcript has both the sense and complementary antisense nucleic acid sequences of the target gene, e.g., a hairpin. The siRNA may either be a dsRNA or shRNA.

As used herein, the term "dsRNA" refers to a construct of two RNA molecules having complementary sequences to one another and that have annealed together via the complementary sequences to form a double-stranded RNA molecule. The nucleotide sequence of two strands may include not only the "sense" or "antisense" RNAs selected from a protein coding sequence of target gene sequence, but also RNA molecule having a nucleotide sequence selected from non-coding rigion of the target gene.

The term "shRNA", as used herein, refers to an siRNA having a stem-loop structure, including a first and second regions complementary to one another, i.e., sense and antisense strands. The degree of complementarity and orientation of the regions are sufficient such that base pairing occurs between the regions, the first and second regions are joined by a loop region, and the loop results from a lack of base pairing between nucleotides (or nucleotide analogs) within the loop region. The loop region of an shRNA is a single-stranded region intervening between the sense and antisense strands and may also be referred to as "intervening single-strand".

As use herein, the term "siD/R-NA" refers to a double-stranded polynucleotide molecule which is composed of both RNA and DNA, and includes hybrids and chimeras of RNA and DNA and prevents translation of a target mRNA. Herein, a hybrid indicates a molecule wherein a polynucleotide composed of DNA and a polynucleotied composed of RNA hybridize to each other to form the double-stranded molecule; whereas a chimera indicates that one or both of the strands composing the double stranded molecule may contain RNA and DNA. Standard techniques of introducing siD/R-NA into the cell are used. The siD/R-NA includes a sense nucleic acid sequence (also referred to as "sense strand") of the STC2 gene, a antisense nucleic acid sequence (also referred to as "antisense strand") of the STC2 gene or both. The siD/R-NA may be constructed such that a single transcript has both the sense and complementary antisense nucleic acid sequences from the target gene, e.g., a hairpin. The siD/R-NA may either be a dsD/R-NA or shD/R-NA.

As used herein, the term "dsD/R-NA" refers to a construct of two molecules having complementary sequences to one another and that have annealed together via the complementary sequences to form a double-stranded polynucleotide molecule. The nucleotide sequence of two strands may include not only the "sense" or "antisense" polynucleotides sequence selected from a protein coding sequence of target gene sequence, but also polynucleotide having a nucleotide sequnence selected from non-coding region of the target gene. One or both of the two molecules constructing the dsD/R-NA are composed of both RNA and DNA (chimeric molecule), or alternatively, one of the molecules is composed of RNA and the other is composed of DNA (hybrid double-strand).

The term "shD/R-NA", as used herein, refers to an siD/R-NA having a stem-loop structure, having a first and second regions complementary to one another, i.e., sense and antisense strands. The degree of complementarity and orientation of the regions are sufficient such that base pairing occurs between the regions, the first and second regions are joined by a loop region, and the loop results from a lack of base pairing between nucleotides (or nucleotide analogs) within the loop region. The loop region of an shD/R-NA is a single-stranded region intervening between the sense and antisense strands and may also be referred to as "intervening single-strand".

As used herein, an "isolated nucleic acid" is a nucleic acid removed from its original environment (e.g., the natural environment if naturally occurring) and thus, synthetically altered from its natural state. In the context of the present invention, examples of isolated nucleic acid includes DNA, RNA, and derivatives thereof.

A double-stranded molecule targeting the STC2 gene molecule that hybridizes to the mRNA of the STC2 gene, decreases or inhibits production of the STC2 protein encoded by the STC2 gene by associating with the normally single-stranded mRNA transcript of the gene, thereby interfering with translation and thus, inhibiting expression of the protein.

The double-stranded molecule serves as a guide for identifying homologous sequences in mRNA for the RISC complex, when the double-stranded molecule is introduced into cells. The identified target RNA is cleaved and degraded by the nuclease activity of Dicer, through which the double-stranded molecule eventually decreases or inhibits production (expression) of the polypeptide encoded by the RNA. Thus, a double-stranded molecule of the present invention can be defined by its ability to generate a single-strand that specifically hybridizes to the mRNA of the STC2 gene under stringent conditions. Herein, the portion of the mRNA that hybridizes with the single-strand generated from the double-stranded molecule is referred to as "target sequence" or "target nucleic acid" or "target nucleotide". In the present invention, nucleotide sequence of the "target sequence" can be shown using not only the RNA sequence of the mRNA, but also the DNA sequence of cDNA synthesized from the mRNA.

In the context of the present invention, the target sequence of a double-stranded molecule is preferably less than 500, 200, 100, 50, or 25 base pairs in length. More preferably, the target sequences of a double-stranded is 19-25 base pairs in length. Accordingly, the present invention provides the double-stranded molecules having a sense strand and an antisense strand, wherein the sense strand includes a nucleotide sequence corresponding to a target sequence. In preferable embodiments, the sense strand hybridizes with antisense strand at the target sequence to form the double-stranded molecule having between 19 and 25 nucleotide pair in length.

Exemplary target nucleotide sequences of double-stranded molecules targeting the STC2 gene includes the nucleotide sequences of SEQ ID NO: 8 or 9. The nucleotide "t" in the sequence should be replaced with "u" in RNA or derivatives thereof. Accordingly, for example, double-stranded molecules of the present invention can include the nucleotide sequence:
5'-GACGAACAGTCTGAGTATT-3' (SEQ ID NO: 8) or
5'-GCAGGAGCTGGTATTGTAG-3' (SEQ ID NO: 9) as a target sequence.

In order to enhance the inhibition activity of the double-stranded molecule, nucleotide "u", "t" or other nucleotide can be added to the 3'end of the target sequence in the antisense strand and/or sense strand. The number of nucleotides to be added is at least 2, generally 2 to 10, preferably 2 to 5. The added nucleotides form a single strand at the 3'end of the antisense strand and/or sense strand of the double-stranded molecule.

Other target sequences of suitable double-stranded molecules for the present invention can be designed using an siRNA design computer program available from the Ambion website (world-wide web.ambion.ambion.com/techlib/misc/siRNA_finder.html). The computer program selects target sequences for double-stranded molecules based on the following protocol.

Selection of Target Sites:
1. Beginning with the AUG start codon of the object transcript, scan downstream for AA dinucleotide sequences. Record the occurrence of each AA and the 3' adjacent 19 nucleotides as potential siRNA target sites. Tuschl et al. Genes Cev 1999, 13(24):3191-7 don't recommend designing siRNA to the 5' and 3' untranslated regions (UTRs) and regions near the start codon (within 75 nucleotides) as these may be richer in regulatory protein binding sites. UTR-binding proteins and/or translation initiation complexes may interfere with binding of the siRNA endonuclease complex.
2. Compare the potential target sites to the human genome database and eliminate from consideration any target sequences with significant homology to other coding sequences. The homology search can be performed using BLAST (Altschul S F et al., Nucleic Acids Res 1997, 25:3389-402; J Mol Biol 1990, 215:403-10), which can be found on the NCBI server at: world-wide web.ncbi.nlm.nih.gov/BLAST/.
3. Select qualifying target sequences for synthesis. At Ambion, preferably several target sequences can be selected along the length of the gene to evaluate.

The double-stranded molecule of the present invention is directed to a single target sequence or may be directed to a plurality of target sequences.

A target sequence for the STC2 gene is meant a nucleotide sequence that is identical to a portion of the STC2 gene (i.e, a polynucleotide within the STC2 gene that is equal in length to and complementary to an double-stranded molecule). The target sequence can include the 5' untranslated (UT) region, the open reading frame (ORF) or the 3' untranslated region of the STC2 gene. Alternatively, the double-stranded molecule can be a nucleic acid sequence complementary to an upstream or downstream modulator of the STC2 gene expression. Examples of upstream and downstream modulators include, a transcription factor that binds the STC2 gene promoter, a kinase or phosphatase that interacts with the STC2 polypeptide, a promoter or enhancer of the STC2 gene.

A double-stranded molecule of the present invention targeting the above-mentioned targeting sequence of the STC2 gene include isolated polynucleotides that includes any of the nucleic acid sequences of target sequences and/or complementary sequences to the target sequences. Examples of polynucleotides targeting the STC2 gene include those having the sequence of SEQ ID NO: 8 or 9 and/or complementary sequences to these nucleotides. However, the present invention is not limited to these examples, and minor modifications in the aforementioned nucleic acid sequences are acceptable so long as the modified molecule retains the ability to suppress the expression of the STC2 gene. Herein, "minor modification" in a nucleic acid sequence indicates one, two or several substitutions, deletions, additions or insertions of nucleic acids to the sequence. Typically, a minor modification will be four or fewer, sometimes three or fewer, and often two or fewer substitutions, deletions, additions or insertions of nucleic acids to the sequence.

According to the present invention, a double-stranded molecule of the present invention can be tested for its ability using the methods utilized in the Examples. In the Examples, the double-stranded molecules having sense strands or antisense strands complementary thereto of three portions of mRNA of the STC2 genes were tested in vitro for their ability to decrease production of the STC2 gene product in prostate cancer cell line according to standard methods. Furthermore, for example, reduction in the STC2 gene product in cells contacted with the candidate double-stranded molecule as compared to cells cultured in the absence of the candidate molecule can be detected by, e.g. RT-PCR using primers for STC2 mRNA mentioned under Example 1, item "Semi-quantitative RT-PCR". Sequences that decrease the production of the STC2 gene product in in vitro cell-based assays can then be tested for their inhibitory effects on cell growth. Sequences that inhibit cell growth in in vitro cell-based assay can then be tested for their in vivo ability using animals with cancer, e.g. nude mouse xenograft models, to confirm decreased production of the STC2 gene product and decreased cancer cell growth.

When the isolated polynucleotide is RNA or derivatives thereof, base "t" should be replaced with "u" in the nucleotide sequences. As used herein, the term "complementary" refers to Watson-Crick or Hoogsteen base pairing between nucleotides units of a polynucleotide, and the term "binding" means the physical or chemical interaction between two polynucleotides. When the polynucleotide includes modified nucleotides and/or non-phosphodiester linkages, these polynucleotides may also bind each other as same manner. Generally, complementary polynucleotide sequences hybridize under appropriate conditions to form stable duplexes containing few or no mismatches. Furthermore, the sense strand and antisense strand of the isolated polynucleotide of the present invention can form double-stranded molecule or hairpin loop structure by the hybridization. In a preferred embodiment, such duplexes contain no more than 1 mismatch for every 10 matches. In an especially preferred embodiment, where the strands of the duplex are fully complementary, such duplexes contain no mismatches.

The double-stranded molecules of the present invention may contain one or more modified nucleotides and/or non-phosphodiester linkages. Chemical modifications well known in the art are capable of increasing stability, availability, and/or cell uptake of the double-stranded molecule. The skilled person will be aware of other types of chemical modification which may be incorporated into the present molecules (WO03/070744; WO2005/045037). In one embodiment, modifications can be used to provide improved resistance to degradation or improved uptake. Examples of such modifications include phosphorothioate linkages, 2'-O-methyl ribonucleotides (especially on the sense strand of a double-stranded molecule), 2'-deoxy-fluoro ribonucleotides, 2'-deoxy ribonucleotides, "universal base" nucleotides, 5'-C— methyl nucleotides, and inverted deoxyabasic residue incorporation (US20060122137). In another embodiment, modifications can be used to enhance the stability or to increase targeting efficiency of the double-stranded molecule. Modifications include chemical cross linking between the two complementary strands of a double-stranded molecule, chemical modification of a 3' or 5' terminus of a strand of a double-stranded molecule, sugar modifications, nucleobase modifications and/or backbone modifications, 2-fluoro modified ribonucleotides and 2'-deoxy ribonucleotides (WO2004/029212). In another embodiment, modifications can be used to increased or decreased affinity for the complementary nucleotides in the target mRNA and/or in the complementary double-stranded molecule strand (WO2005/044976). For example, an unmodified pyrimidine nucleotide can be substituted for a 2-thio, 5-alkynyl, 5-methyl, or 5-propynyl pyrimidine. Additionally, an unmodified purine can be substituted with a 7-deaza, 7-alkyl, or 7-alkenyl purine. In another embodiment, when the double-stranded molecule is a double-stranded molecule with a 3' overhang, the 3'-terminal nucleotide overhanging nucleotides may be replaced by deoxyribonucleotides (Elbashir S M et al., Genes Dev 2001 Jan. 15, 15(2): 188-200). For further details, published documents such as US20060234970 are available. The present invention is not limited to these examples and any known chemical modifications may be employed for the double-stranded molecules of the present invention so long as the resulting molecule retains the ability to inhibit the expression of the target gene. Furthermore, the double-stranded molecules of the present invention may include both DNA and RNA, e.g., dsD/R-NA or shD/R-NA. Specifically, a hybrid polynucleotide of a DNA strand and an RNA strand or a DNA-RNA chimera polynucleotide shows increased stability. Mixing of DNA and RNA, i.e., a hybrid type double-stranded molecule composed of a DNA strand (polynucleotide) and an RNA strand (polynucleotide), a chimera type double-stranded molecule including both DNA and RNA on any or both of the single strands (polynucleotides), or the like may be formed for enhancing stability of the double-stranded molecule.

The hybrid of a DNA strand and an RNA strand may be either where the sense strand is DNA and the antisense strand is RNA, or vice versa, so long as it has an activity to inhibit expression of the target gene when introduced into a cell expressing the gene. Preferably, the sense strand polynucleotide is DNA and the antisense strand polynucleotide is RNA. Also, the chimera type double-stranded molecule may be either where both of the sense and antisense strands are composed of DNA and RNA, or where any one of the sense and antisense strands is composed of DNA and RNA so long as it has an activity to inhibit expression of the target gene when introduced into a cell expressing the gene. In order to enhance stability of the double-stranded molecule, the molecule preferably contains as much DNA as possible, whereas to induce inhibition of the target gene expression, the molecule is required to be RNA within a range to induce sufficient inhibition of the expression. As a preferred example of the chimera type double-stranded molecule, an upstream partial region (i.e., a region flanking to the target sequence or complementary sequence thereof within the sense or antisense strands) of the double-stranded molecule is RNA. Preferably, the upstream partial region indicates the 5' side (5'-end) of the sense strand and the 3' side (3'-end) of the antisense strand. Alternatively, regions flanking to 5'-end of sense strand and/or 3'-end of antisense strand are referred to upstream partial region. That is, in preferable embodiments, a region flanking to the 3'-end of the antisense strand, or both of a region flanking to the 5'-end of sense strand and a region flanking to the 3'-end of antisense strand composed of RNA. For instance, the chimera or hybrid type double-stranded molecule of the present invention include following combinations.

```
sense strand:
5'-[---DNA---]-3'
3'-(RNA)-[DNA]-5'
:antisense strand, sense strand:
5'-(RNA)-[DNA]-3'
3'-(RNA)-[DNA]-5'
:antisense strand,
and sense strand:
5'-(RNA)-[DNA]-3'
3'-(---RNA---)-5'
:antisense strand.
```

The upstream partial region preferably is a domain composed of 9 to 13 nucleotides counted from the terminus of the target sequence or complementary sequence thereto within the sense or antisense strands of the double-stranded molecules. Moreover, preferred examples of such chimera type double-stranded molecules include those having a strand length of 19 to 21 nucleotides in which at least the upstream half region (5' side region for the sense strand and 3' side region for the antisense strand) of the polynucleotide is RNA and the other half is DNA. In such a chimera type double-stranded molecule, the effect to inhibit expression of the target gene is much higher when the entire antisense strand is RNA (US20050004064).

In the context of the present invention, the double-stranded molecule may form a hairpin, such as a short hairpin RNA (shRNA) and short hairpin composed of DNA and RNA (shD/R-NA). The shRNA or shD/R-NA is a sequence of RNA or mixture of RNA and DNA making a tight hairpin turn that can be used to silence gene expression via RNA interference. The shRNA or shD/R-NA may include the sense target sequence and the antisense target sequence on a single strand wherein the sequences are separated by a loop sequence. Generally, the hairpin structure is cleaved by the cellular machinery into dsRNA or dsD/R-NA, which is then bound to the RNA-induced silencing complex (RISC). This complex binds to and cleaves mRNAs which match the target sequence of the dsRNA or dsD/R-NA.

A loop sequence composed of an arbitrary nucleotide sequence can be located between the sense and antisense strands in order to form a hairpin loop structure. Thus, the double-stranded molecule contained in the inventive composition may take the general formula 5'-[A]-[B]-[A']-3', wherein [A] is the sense strand having a target sequence, [B] is an intervening single-strand and [A'] is the antisense strand having a complementary sequence to [A]. The target sequence may be selected from group composed of, for example, nucleotide sequences shown in SEQ ID NO:8 and SEQ ID NO 9.

The present invention is not limited to these examples, and the target sequence in [A] may be modified sequences from these examples so long as the double-stranded molecule retains the ability to suppress the expression of the targeted PKIB or NAALADL2 gene. The region [A] hybridizes to [A'] to form a loop composed of the region [B]. The intervening single-stranded portion [B], i.e., loop sequence may be preferably 3 to 23 nucleotides in length. The loop sequence, for example, can be selected from group composed of following sequences (world wide web.ambion.com/techlib/tb/tb_506.html). Furthermore, loop sequence composed of 23 nucleotides also provides active siRNA (Jacque J M et al., Nature 2002 Jul. 25, 418(6896): 435-8, Epub 2002 Jun. 26): CCC, CCACC, or CCACACC: Jacque J M et al., Nature 2002 Jul. 25, 418(6896): 435-8, Epub 2002 Jun. 26;

UUCG: Lee N S et al., Nat Biotechnol 2002 May, 20(5): 500-5; Fruscoloni P et al., Proc Natl Acad Sci USA 2003 Feb. 18, 100(4): 1639-44, Epub 2003 Feb. 10; and UUCAAGAGA: Dykxhoorn D M et al., Nat Rev Mol Cell Biol 2003 June, 4(6): 457-67. Exemplary, preferable double-stranded molecules having hairpin loop structure of the present invention are shown below. In the following structure, the loop sequence can be selected from group composed of AUG, CCC, UUCG, CCACC, CTCGAG, AAGCUU, CCACACC, and UUCAAGAGA; however, the present invention is not limited thereto:

```
5'-GACGAACAGUCUGAGUAUU-[B]-AAUACUCAGACUGUUCGUC-3';
(for target sequence of SEQ ID NO: 8)
and 5'-GCAGGAGCUGGUAUUGUAG-[B]-CUACAAUACCAGCUCCUGC-3'.
(for target sequence of SEQ ID NO: 9)
```

The method of preparing the double-stranded molecule is not particularly limited but it is preferable to use a chemical synthetic method known in the art. According to the chemical synthesis method, sense and antisense single-stranded polynucleotides are separately synthesized and then annealed together via an appropriate method to obtain a double-stranded molecule. Specific example for the annealing includes wherein the synthesized single-stranded polynucleotides are mixed in a molar ratio of preferably at least about 3:7, more preferably about 4:6, and most preferably substantially equimolar amount (i.e., a molar ratio of about 5:5). Next, the mixture is heated to a temperature at which double-stranded molecules dissociate and then is gradually cooled down. The annealed double-stranded polynucleotide can be purified by usually employed methods known in the art. Example of purification methods include methods utilizing agarose gel electrophoresis or wherein remaining single-stranded polynucleotides are optionally removed by, e.g., degradation with appropriate enzyme.

The regulatory sequences flanking STC2 sequences may be identical or different, such that their expression can be modulated independently, or in a temporal or spatial manner. The double-stranded molecules can be transcribed intracellularly by cloning STC2 gene templates into a vector containing, e.g., a RNA pol III transcription unit from the small nuclear RNA (snRNA) U6 or the human H1 RNA promoter.

IV-2. Vectors Containing a Double-Stranded Molecule of the Present Invention

Also included in the invention are vector compositions containing one or more of the antisense nucleic acids or the double-stranded molecules described herein, and a cell containing the vector. A vector of the present invention preferably encodes an antisense nucleic acid or a double-stranded molecule of the present invention in an expressible form. Herein, the phrase "in an expressible form" indicates that the vector, when introduced into a cell, will express the molecule. In a preferred embodiment, the vector includes regulatory elements necessary for expression of the antisense nucleic acid or the double-stranded molecule. Such vectors of the present invention may be used for producing the present antisense nucleic acids or double-stranded molecules, or directly as an active ingredient for treating cancer.

Alternatively, the present invention provides vectors including each of a combination of polynucleotide having a sense strand nucleic acid and an antisense strand nucleic acid, wherein said sense strand nucleic acid has the nucleotide sequence of SEQ ID NO: 8 or 9, and said antisense strand nucleic acid has a sequence complementary to the sense strand, wherein the transcripts of said sense strand and said antisense strand hybridize to each other to form a double-stranded molecule, and wherein said vectors, when introduced into a cell expressing the STC2 gene, inhibits expression of said gene. Preferably, the polynucleotide is an oligonucleotide of between about 19 and 25 nucleotides pair in length (e.g., contiguous nucleotides from the nucleotide sequence of SEQ ID NO: 11). More preferably, the combination of polynucleotide includes a single oligonucleotide transcript including the sense strand and the antisense strand linked via a single-stranded nucleotide sequence. More preferably, the combination of polynucleotide has the general formula 5'-[A]-[B]-[A]-3', wherein [A] is the nucleotide sequence of SEQ ID NO: 8 or 9; [B] is a nucleotide sequence composed of about 3 to about 23 nucleotide; and [A'] is a nucleotide sequence complementary to [A]. Vectors of the present invention can be produced, for example, by cloning STC2 gene into an expression vector so that regulatory sequences are operatively-linked to STC2 gene sequence in a manner to allow expression (by transcription of the DNA molecule) of an antisense nucleic acid or both strands of a double-stranded molecule (Lee N S et al., Nat Biotechnol 2002 May, 20(5): 500-5).

For example, in double-stranded molecules, RNA molecule that is the antisense to mRNA is transcribed by a first promoter (e.g., a promoter sequence flanking to the 3' end of the cloned DNA) and RNA molecule that is the sense strand to the mRNA is transcribed by a second promoter (e.g., a promoter sequence flanking to the 5' end of the cloned DNA). The sense and antisense strands hybridize in vivo to generate a double-stranded molecule constructs for silencing of the gene. Alternatively, two vectors constructs respectively encoding the sense and antisense strands of the double-stranded molecule are utilized to respectively express the sense and anti-sense strands and then forming a double-stranded molecule construct. Furthermore, the cloned sequence may encode a construct having a secondary structure (e.g., hairpin); namely, a single transcript of a vector contains both the sense and complementary antisense sequences of the target gene.

The vectors of the present invention may also be equipped so to achieve stable insertion into the genome of the target cell (see, e.g., Thomas K R & Capecchi M R, Cell 1987, 51: 503-12 for a description of homologous recombination cassette vectors). See, e.g., Wolff et al., Science 1990, 247: 1465-8; U.S. Pat. Nos. 5,580,859; 5,589,466; 5,804,566; 5,739,118; 5,736,524; 5,679,647; and WO 98/04720. Examples of DNA-based delivery technologies include "naked DNA", facilitated (bupivicaine, polymers, peptide-mediated) delivery, cationic lipid complexes, and particle-mediated ("gene gun") or pressure-mediated delivery (see, e.g., U.S. Pat. No. 5,922,687).

The vectors of the present invention may be, for example, viral or bacterial vectors. Examples of expression vectors include attenuated viral hosts, such as vaccinia or fowlpox (see, e.g., U.S. Pat. No. 4,722,848). This approach involves the use of vaccinia virus, e.g., as a vector to express nucleotide sequences that encode the antisense nucleic acid or the double-stranded molecule. Upon introduction into a cell expressing the target gene, the recombinant vaccinia virus expresses the molecule and thereby suppresses the proliferation of the cell. Another example of useable vector includes Bacille Calmette Guerin (BCG). BCG vectors are described in Stover et al., Nature 1991, 351: 456-60. A wide variety of other vectors are useful for therapeutic administration and production of the antisense nucleic acids or the double-stranded molecules; examples include adeno and adeno-associated virus vectors, retroviral vectors, *Salmonella typhi* vectors, detoxified anthrax toxin vectors, and the like. See, e.g., Shata et al., Mol Med Today 2000, 6: 66-71; Shedlock et al., J Leukoc Biol 2000, 68: 793-806; and Hipp et al., In Vivo 2000, 14: 571-85.

IV-3. Methods for Treating or Preventing Cancer Using a Double-Stranded Molecule of the Present Invention:

In present invention, two different double-stranded molecules targeting the STC2 gene could effectively knocked down the expression of the gene in lung cancer cell lines coincided with suppression of cell proliferation (Example 4).

Accordingly, the present invention provides methods for inhibiting cell growth, i.e., prostate cancer cell growth, by inducing dysfunction of the STC2 gene via inhibiting the expression of the STC2 gene. STC2 gene expression can be inhibited by the aforementioned double-stranded molecules of the present invention that specifically target of the STC2 gene or the vectors of the present invention that can express the double-stranded molecules.

Such ability of the present double-stranded molecules and vectors to inhibit cell growth of cancerous cell indicates that they can be used for methods for treating cancer. Thus, the present invention provides methods to treat patients with prostate cancer by administering a double-stranded molecule against STC2 gene or a vector expressing thereof without adverse effect because that genes were hardly detected in normal organs. In the preferred embodiment of the present invention, the prostate cancer is CRPC or aggressive PC (e.g., Gleason score 8-10).

The growth of cells expressing a STC2 gene may be inhibited by contacting the cells with a double-stranded molecule against a STC2 gene, a vector expressing the molecule or a composition containing the same. The cell may be further contacted with a transfection agent. Suitable transfection agents are known in the art. The phrase "inhibition of cell growth" indicates that the cell proliferates at a lower rate or has decreased viability as compared to a cell not exposed to the molecule. Cell growth may be measured by methods known in the art, e.g., using the MTT cell proliferation assay.

Thus, patients suffering from or at risk of developing disease related to STC2 gene may be treated with an administration of at least one of the present double-stranded molecules, at least one vector expressing at least one of the molecules or at least one composition containing at least one of the molecules. For example, patients suffering from prostate cancer may be treated according to the present methods. The type of cancer may be identified by standard methods according to the particular type of tumor to be diagnosed. Prostate cancer may be diagnosed, for example, with PSA, as prostate cancer marker. Alternatively, the diagnosing method of the present invention described in the item "I. Diagnosing cancer" may be used for identifying prostate cancer. In the preferred embodiment of the present invention, patients to be treated by the methods of the present invention are selected by detecting the expression level of STC2 gene in a biopsy specimen from the patient. Preferably, before the treatment of the present invention, the biopsy specimen from the subject is confirmed for STC2 gene over-expression by methods known in the art, for example, immunohistochemical analysis or RT-PCR.

According to the present method to inhibit cell growth and thereby treat cancer, through the administration of plural kinds of the double-stranded molecules (or vectors expressing or compositions containing the same), each of the molecules may have different structures but act at mRNA that matches the same target sequence of STC2 gene. Alternatively plural kinds of the double-stranded molecules may act on at mRNA that matches different target sequence of same gene. For example, the method may utilize double-stranded molecules directed to STC2 gene.

For inhibiting cell growth, a double-stranded molecule of the present invention may be directly introduced into the cells in a form to achieve binding of the molecule with corresponding mRNA transcripts. Alternatively, as described above, a DNA encoding the double-stranded molecule may be introduced into cells as a vector. For introducing the double-stranded molecules and vectors into the cells, transfection-enhancing agent, such as FuGENE (Roche diagnostics), Lipofectamine 2000 (Invitrogen), Oligofectamine (Invitrogen), and Nucleofector (Wako pure Chemical), may be employed.

A treatment is deemed "efficacious" if it leads to clinical benefit such as, reduction in expression of STC2 gene, or a decrease in size, prevalence, or metastatic potential of the cancer in the subject. When the treatment is applied prophylactically, "efficacious" means that it retards or prevents cancers from forming or prevents or alleviates a clinical symptom of cancer. Efficaciousness is determined in association with any known method for diagnosing or treating the particular tumor type. To the extent that the methods and compositions of the present invention find utility in the context of "prevention" and "prophylaxis", such terms are interchangeably used herein to refer to any activity that reduces the burden of mortality or morbidity from disease. Prevention and prophylaxis can occur "at primary, secondary and tertiary prevention levels." While primary prevention and prophylaxis avoid the development of a disease, secondary and tertiary levels of prevention and prophylaxis encompass activities aimed at the prevention and prophylaxis of the progression of a disease and the emergence of symptoms as well as reducing the negative impact of an already established disease by restoring function and reducing disease-related complications. Alternatively, prevention and prophylaxis can include a wide range of prophylactic therapies aimed at alleviating the severity of the particular disorder, e.g. reducing the proliferation and metastasis of tumors.

The treatment and/or prophylaxis of cancer and/or the prevention of postoperative recurrence thereof include any of the following steps, such as the surgical removal of cancer cells, the inhibition of the growth of cancerous cells, the involution or regression of a tumor, the induction of remission and suppression of occurrence of cancer, the tumor regression, and the reduction or inhibition of metastasis. Effectively treating and/or the prophylaxis of cancer decreases mortality and improves the prognosis of individuals having cancer, decreases the levels of tumor markers in the blood, and alleviates detectable symptoms accompanying cancer. For example, reduction or improvement of symptoms constitutes effectively treating and/or the prophylaxis include 10%, 20%, 30% or more reduction, or stable disease.

It is understood that a double-stranded molecule of the present invention degrades the target mRNA in sub-stoichiometric amounts. Without wishing to be bound by any theory, it is believed that the double-stranded molecule of the present invention causes degradation of the target mRNA in a catalytic manner. Thus, as compared to standard cancer therapies, the present invention requires the delivery of significantly less double-stranded molecule at or near the site of cancer in order to exert therapeutic effect.

One skilled in the art can readily determine an effective amount of the double-stranded molecule of the present invention to be administered to a given subject, by taking into account factors such as body weight, age, sex, type of disease, symptoms and other conditions of the subject; the route of administration; and whether the administration is regional or systemic. Generally, an effective amount of the double-stranded molecule of the present invention is an intercellular concentration at or near the cancer site of from about 1 nanomolar (nM) to about 100 nM, preferably from about 2 nM to about 50 nM, more preferably from about 2.5 nM to about 10 nM. It is contemplated that greater or smaller amounts of the double-stranded molecule can be administered. The precise dosage required for a particular circumstance may be readily and routinely determined by one of skill in the art.

The present methods can be used to inhibit the growth or metastasis of cancer expressing STC2 gene; for example prostate cancer, especially CRPC or aggressive PC (e.g., Gleason score 8-10). In particular, a double-stranded molecule containing a target sequence of SEQ ID NO: 8 or 9 is particularly preferred for the treatment of prostate cancer.

For treating cancer, the double-stranded molecule of the present invention can also be administered to a subject in combination with a pharmaceutical agent different from the double-stranded molecule. Alternatively, the double-stranded molecule of the present invention can be administered to a subject in combination with another therapeutic method designed to treat cancer. For example, the double-stranded molecule of the present invention can be administered in combination with therapeutic methods currently employed for treating cancer or preventing cancer metastasis (e.g., radiation therapy, surgery and treatment using chemotherapeutic agents).

In the present methods, the double-stranded molecule can be administered to the subject either as a naked double-stranded molecule, in conjunction with a delivery reagent, or as a recombinant plasmid or viral vector which expresses the double-stranded molecule.

Suitable delivery reagents for administration in conjunction with the present a double-stranded molecule include the Mirus Transit TKO lipophilic reagent; lipofectin; lipofectamine; cellfectin; or polycations (e.g., polylysine), or liposomes. A preferred delivery reagent is a liposome.

Liposomes can aid in the delivery of the double-stranded molecule to a particular tissue, such as prostate tissue, and can also increase the blood half-life of the double-stranded molecule. Liposomes suitable for use in the context of the present invention may be formed from standard vesicle-forming lipids, which generally include neutral or negatively charged phospholipids and a sterol, such as cholesterol. The selection of lipids is generally guided by consideration of factors such as the desired liposome size and half-life of the liposomes in the blood stream. A variety of methods are known for preparing liposomes, for example as described in Szoka et al., Ann Rev Biophys Bioeng 1980, 9: 467; and U.S. Pat. Nos. 4,235,871; 4,501,728; 4,837,028; and 5,019,369, the entire disclosures of which are herein incorporated by reference.

Preferably, the liposomes encapsulating the present double-stranded molecule includes a ligand molecule that can deliver the liposome to the cancer site. Ligands which bind to receptors prevalent in tumor or vascular endothelial cells, such as monoclonal antibodies that bind to tumor antigens or endothelial cell surface antigens, are preferred.

Particularly preferably, the liposomes encapsulating the present double-stranded molecule are modified so as to avoid clearance by the mononuclear macrophage and reticuloendothelial systems, for example, by having opsonization-inhibition moieties bound to the surface of the structure. In one embodiment, a liposome of the invention can include both opsonization-inhibition moieties and a ligand.

Opsonization-inhibiting moieties for use in preparing the liposomes of the invention are typically large hydrophilic polymers that are bound to the liposome membrane. As used herein, an opsonization inhibiting moiety is "bound" to a liposome membrane when it is chemically or physically attached to the membrane, e.g., by the intercalation of a lipid-soluble anchor into the membrane itself, or by binding directly to active groups of membrane lipids. These opsonization-inhibiting hydrophilic polymers form a protective surface layer which significantly decreases the uptake of the liposomes by the macrophage-monocyte system ("MMS") and reticuloendothelial system ("RES"); e.g., as described in U.S. Pat. No. 4,920,016, the entire disclosure of which is herein incorporated by reference. Liposomes modified with opsonization-inhibition moieties thus remain in the circulation much longer than unmodified liposomes. For this reason, such liposomes are sometimes called "stealth" liposomes. Stealth liposomes are known to accumulate in tissues fed by porous or "leaky" microvasculature. Thus, target tissue characterized by such microvasculature defects, for example, solid tumors, will efficiently accumulate these liposomes; see Gabizon et al., Proc Natl Acad Sci USA 1988, 18: 6949-53. In addition, the reduced uptake by the RES lowers the toxicity of stealth liposomes by preventing significant accumulation in liver and spleen. Thus, liposomes of the invention that are modified with opsonization-inhibition moieties can deliver the present double-stranded molecule to prostate cancer cells.

Opsonization inhibiting moieties suitable for modifying liposomes are preferably water-soluble polymers with a molecular weight from about 500 to about 40,000 daltons, and more preferably from about 2,000 to about 20,000 daltons. Such polymers include polyethylene glycol (PEG) or polypropylene glycol (PPG) derivatives; e.g., methoxy PEG or PPG, and PEG or PPG stearate; synthetic polymers such as polyacrylamide or poly N-vinyl pyrrolidone; linear, branched, or dendrimeric polyamidoamines; polyacrylic acids; polyalcohols, e.g., polyvinylalcohol and polyxylitol to which carboxylic or amino groups are chemically linked, as well as gangliosides, such as ganglioside GM.sub.1. Copolymers of PEG, methoxy PEG, or methoxy PPG, or derivatives thereof, are also suitable. In addition, the opsonization inhibiting polymer can be a block copolymer of PEG and either a polyamino acid, polysaccharide, polyamidoamine, polyethyleneamine, or polynucleotide. The opsonization inhibiting polymers can also be natural polysaccharides containing amino acids or carboxylic acids, e.g., galacturonic acid, glucuronic acid, mannuronic acid, hyaluronic acid, pectic acid, neuraminic acid, alginic acid, carrageenan; aminated polysaccharides or oligosaccharides (linear or branched); or carboxylated polysaccharides or oligosaccharides, e.g., reacted with derivatives of carbonic acids with resultant linking of carboxylic groups.

Preferably, the opsonization-inhibiting moiety is a PEG, PPG, or derivatives thereof. Liposomes modified with PEG or PEG-derivatives are sometimes called "PEGylated liposomes".

The opsonization inhibiting moiety can be bound to the liposome membrane by any one of numerous well-known techniques. For example, an N-hydroxysuccinimide ester of PEG can be bound to a phosphatidyl-ethanolamine lipid-soluble anchor, and then bound to a membrane. Similarly, a dextran polymer can be derivatized with a stearylamine lipid-soluble anchor via reductive amination using Na(CN)BH.sub. 3 and a solvent mixture such as tetrahydrofuran and water in a 30:12 ratio at 60 degrees C. Vectors expressing a double-stranded molecule of the present invention are discussed above. Such vectors expressing at least one double-stranded molecule of the invention can also be administered directly or in conjunction with a suitable delivery reagent, including the Mirus Transit LT1 lipophilic reagent; lipofectin; lipofectamine; cellfectin; polycations (e.g., polylysine) or liposomes. Methods for delivering recombinant viral vectors, which express a double-stranded molecule of the invention, to an area of cancer in a patient are within the skill of the art.

The double-stranded molecule of the present invention can be administered to the subject by any means suitable for delivering the double-stranded molecule into cancer sites. For example, the double-stranded molecule can be administered by gene gun, electroporation, or by other suitable parenteral or enteral administration routes.

Suitable enteral administration routes include oral, rectal, or intranasal delivery.

Suitable parenteral administration routes include intravesical and intravascular administration (e.g., intravenous bolus injection, intravenous infusion, intra-arterial bolus injection, intra-arterial infusion and catheter instillation into the vasculature); peri- and intra-tissue injection (e.g., peri-tumoral or intra-tumoral injection); subcutaneous injection or deposition including subcutaneous infusion (such as by osmotic pumps); direct application to the area at or near the site of cancer, for example by a catheter or other placement device (e.g., a suppository or an implant including a porous, non-porous, or gelatinous material); and inhalation. It is preferred that injections or infusions of the double-stranded molecule or vector be given at or near the site of the cancer.

The double-stranded molecule of the present invention can be administered in a single dose or in multiple doses. Where the administration of the double-stranded molecule of the present invention is by infusion, the infusion can be a single sustained dose or can be delivered by multiple infusions. Injection of the agent directly into the tissue is at or near the site of cancer preferred. Multiple injections of the agent into the tissue at or near the site of cancer are particularly preferred.

One skilled in the art can also readily determine an appropriate dosage regimen for administering the double-stranded molecule of the invention to a given subject. For example, the double-stranded molecule can be administered to the subject once, for example, as a single injection or deposition at or near the cancer site. Alternatively, the double-stranded molecule can be administered once or twice daily to a subject for a period of from about three to about twenty-eight days, more preferably from about seven to about ten days. In a preferred dosage regimen, the double-stranded molecule is injected at or near the site of cancer once a day for seven days. Where a dosage regimen includes multiple administrations, it is understood that the effective amount of a double-stranded molecule administered to the subject can include the total amount of a double-stranded molecule administered over the entire dosage regimen.

IV-4 Compositions Containing a Double-Stranded Molecule of the Present Invention:

In addition to the above, the present invention also provides pharmaceutical compositions that include at least one of the present double-stranded molecules or the vectors coding for the molecules.

The double-stranded molecules of the present invention are preferably formulated as pharmaceutical compositions prior to administering to a subject, according to techniques known in the art. Pharmaceutical compositions of the present invention are characterized as being at least sterile and pyrogen-free. As used herein, "pharmaceutical formulations" include formulations for human and veterinary use. Methods for preparing pharmaceutical compositions of the invention are within the skill in the art, for example as described in Remington's Pharmaceutical Science, 17th ed., Mack Publishing Company, Easton, Pa. (1985), the entire disclosure of which is herein incorporated by reference.

The present pharmaceutical formulations contain at least one of the double-stranded molecules or vectors encoding them of the present invention (e.g., 0.1 to 90% by weight), or a physiologically acceptable salt of the molecule, mixed with a physiologically acceptable carrier medium. Preferred physiologically acceptable carrier media are water, buffered water, normal saline, 0.4% saline, 0.3% glycine, hyaluronic acid and the like.

According to the present invention, the composition may contain plural kinds of double-stranded molecules, each of molecules may be directed to the same target sequence, or different target sequences of STC2 gene. For example, compositions may contain double-stranded molecules directed to one, two or more target sequences of STC2 gene.

Furthermore, the present composition may contain a vector coding for one or plural double-stranded molecules. For example, the vector may encode one, two or several kinds of the present double-stranded molecules. Alternatively, the present composition may contain plural kinds of vectors, each of the vectors coding for a different double-stranded molecule.

Moreover, the present double-stranded molecules may be contained as liposomes in the present composition. See under the item of "IV-3. Methods for treating or preventing cancer using a double-stranded molecule of the present invention" for details of liposomes.

Pharmaceutical compositions of the present invention can also include conventional pharmaceutical excipients and/or additives. Suitable pharmaceutical excipients include stabilizers, antioxidants, osmolality adjusting agents, buffers, and pH adjusting agents. Suitable additives include physiologically biocompatible buffers (e.g., tromethamine hydrochloride), additions of chelants (such as, for example, DTPA or DTPA-bisamide) or calcium chelate complexes (for example calcium DTPA, CaNaDTPA-bisamide), or, optionally, additions of calcium or sodium salts (for example, calcium chloride, calcium ascorbate, calcium gluconate or calcium lactate). Pharmaceutical compositions of the invention can be packaged for use in liquid form, or can be lyophilized.

For solid compositions, conventional nontoxic solid carriers can be used; for example, pharmaceutical grades of mannitol, lactose, starch, magnesium stearate, sodium saccharin, talcum, cellulose, glucose, sucrose, magnesium carbonate, and the like.

For example, a solid pharmaceutical composition for oral administration can include any of the carriers and excipients listed above and 10-95%, preferably 25-75%, of one or more double-stranded molecule of the present invention. A pharmaceutical composition for aerosol (inhalational) administration can include 0.01-20% by weight, preferably 1-10% by weight, of one or more double-stranded molecules of the present invention encapsulated in a liposome as described above, and propellant. A carrier can also be included as desired; e.g., lecithin for intranasal delivery.

In addition to the above, the present composition may contain other pharmaceutical active ingredients so long as they do not inhibit the in vivo function of the present double-stranded molecules of the present invention. For example, the composition may contain chemotherapeutic agents conventionally used for treating cancers.

In another embodiment, the present invention provides for the use of the double-stranded nucleic acid molecules of the present invention in manufacturing a pharmaceutical composition for treating a prostate cancer characterized by the expression of STC2 gene. For example, the present invention relates to a use of double-stranded nucleic acid molecule inhibiting the expression of STC2 gene in a cell, which molecule includes a sense strand and an antisense strand complementary thereto, hybridized to each other to form the double-stranded nucleic acid molecule and targets to a sequence selected from among SEQ ID NOs: 8 and 9, for manufacturing a pharmaceutical composition for treating prostate cancer expressing STC2 gene.

The present invention further provides a method or process for manufacturing a pharmaceutical composition for treating a prostate cancer characterized by the expression of STC2 gene, wherein the method or process includes a step for formulating a pharmaceutically or physiologically acceptable carrier with a double-stranded nucleic acid molecule inhibiting the expression of STC2 gene in a cell, which over-expresses the gene, which molecule includes a sense strand and an antisense strand complementary thereto, hybridized to each other to form the double-stranded nucleic acid molecule and targets to a sequence selected from among SEQ ID NOs: 8 and 9 as active ingredients.

In another embodiment, the present invention provides a method or process for manufacturing a pharmaceutical composition for treating a prostate cancer characterized by the expression of STC2 gene, wherein the method or process includes a step for admixing an active ingredient with a pharmaceutically or physiologically acceptable carrier, wherein the active ingredient is a double-stranded nucleic acid molecule inhibiting the expression of STC2 gene in a cell, which over-expresses the gene, which molecule includes a sense strand and an antisense strand complementary thereto, hybridized to each other to form the double-stranded nucleic acid molecule and targets to a sequence selected from among SEQ ID NOs: 8 and 9.

Aspects of the present invention are described in the following examples, which are not intended to limit the scope of the invention described in the claims.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

EXAMPLES

Example 1

General Methods

1. Cell Lines

Human PC cell lines LNCaP, 22Rv1, DU-145, and PC-3 were obtained from American Type Culture Collection (ATCC, Rockville, Md.). LNCaP derived androgen-independent prostate cancer cell line C4-2B was purchased from ViroMed Laboratories (Minnetonka, Minn., USA). All of the cell lines were cultured as monolayers in the following medium: DMEM (Sigma-Aldrich) for 22Rv1, LNCaP, C4-2B and DU-145; and F-12 (GIBCO) for PC-3 with 10% fetal bovine serum and 1% antibiotic/antimycotic solution (Sigma-Aldrich). Cells were maintained in incubators containing humidified air with 5% $CO_2$ at 37 degrees C.

2. Semi-Quantitative RT-PCR

Purification of PC cells and normal prostatic epithelial cells from frozen PC tissues was described previously (Tamura K, et al., Cancer Res 2007, 67, 5117-5125). Total RNA was extracted using RNeasy Kit (QIAGEN, Valencia, Calif.) according to manufacturer's instruction, treated with DNase I (Roche Diagnostic, Mannheim, Germany), and reversely transcribed to single-stranded cDNA using random hexamer or oligo d(T) primer with Superscript reverse transcriptase II (Invitrogen, Carlsbad, Calif.). Appropriate dilutions of each single-strand cDNA were prepared by normalizing cDNA content using beta-actin (ACTB) as a quantitative control, demonstrating PCR reaction using single strand cDNA as PCR templates. The primer sequences employed in the context of the present invention were:

```
ACTB forward:
5'-TTGGCTTGACTCAGGATTTA-3',     (SEQ ID NO: 1)

ACTB reverse:
5'-ATGCTATCACCTCCCCTGTG-3',     (SEQ ID NO: 2)

STC2 forward:
5'-TTACTCCATGAGCCTTCCTTTG-3',   (SEQ ID NO: 3)
and

STC2 reverse:
5'-TCCTGTTGCCTAAATCCGTAGTA-3'.  (SEQ ID NO: 4)
```

The conditions for PCR are followed; initial denaturation at 95 degrees C. for 5 min, 23 cycles for ACTB and 30 cycles for STC2 of denaturation at 95 degrees C. for 30 sec, annealing at 55 degrees C. for 30 sec, and elongation at 72 degrees C. for 30 sec on a GeneAmp PCR system 9700 (PE Applied Biosystems, Foster, Calif.). Quantitative real-time PCR was also carried out using a PRISM 7700 sequence detector with the SYBR Premix ExTaq (TaKaRa) in accordance with the manufacturer's instructions. The primers for real-time quantitative PCR were the same with those described above.

3. Northern Blot Analysis

Total RNA from five PC cell lines were extracted using RNeasy Kit (QIAGEN, Valencia, Calif.), and their mRNAs were purified using the mRNA Purification Kit (GE Healthcare, Piscataway, N.J., USA), according to the manufacturer's protocols. One-micro gram aliquot of each mRNA from the PC cell lines, as well as those isolated from normal human brain, heart, kidney, liver, lung, prostate and testis (BD Bioscience, Palo Alto, Calif.), were separated on 1% denaturing agarose gels and transferred onto nylon membranes. The membranes were hybridized for 20 hours with $^{32}$P-labeled STC2 cDNA, which was labeled by Megaprime DNA labeling system (GE Bioscience, UK). Probe cDNA of STC2 was prepared as a 551-bp PCR product by using the primers followings:

```
5'-AACATTTACCATTAGAGAGGGGG-3'   (SEQ ID NO: 5)
and

5'-CACATAGAAATGACACTCCTCCC-3'.  (SEQ ID NO: 6)
```

Pre-hybridization, hybridization, and washing were performed according to the manufacturer's instruction. The blots were autoradiographed at −80 degrees C. for 7 days.

4. Generating Monoclonal Antibody to STC2 and Immunohistochemical Analysis

Monoclonal mouse antibodies to STC2 were generated by immunizing recombinant STC2 proteins in MBL (Nagoya, Japan). Castration-naive PC(CNPC) tissues were obtained from the patients who underwent prostectomy in Kochi University Medical School. CRPC tissues were obtained in Kochi University Medical School, Iwate Medical Collage, and Okayama University Medical School under the appropriate informed consents. Immunohistochemical study was carried out using the Ventana automated immunohistochemical systems (Discovery, Ventana Medical systems, Inc., Tucson, Ariz.). Sections were incubated with a 1:100 diluted solution of purified anti-STC2 mAb (0.75 mg/ml), for 16 minutes. The automated protocol is based on an indirect biotin-avidin system using a biotinylated universal secondary antibody and diaminobenzidine substrate with hematoxylin counterstaining. The specificity of the binding was confirmed by negative staining using mouse nonimmune serum as primary antibody.

5. Scoring of Immunohistochemical Staining

To evaluate both the intensity of staining and proportion of the positive-stained cells, a scoring method previously reported was used (Ashida S, et al., Clin Cancer Res 2006, 2767-73). Regarding the morphology and the intensity of STC2 expression, positive staining of anti-STC2 antibody was defined as follows: score 1 for variable weak cytoplasmic staining, score 2 for segmental and apical granular cytoplasmic staining, and score 3 for diffuse continuous and intense cytoplasmic staining. For each score, the proportion of cells with the score was estimated visually. A combined weighed score (STC2 immunohistochemical score) composed of the sum of the proportion of cells with each score was calculated for each sample as described previously (Ashida S, et al., Clin Cancer Res 2006, 2767-73). For example, a case with 70% score 3 staining, 20% score 2 staining, and 10% score 1 staining would be scored as follows: 70×3+20×2+10×1=260. The maximum score should be 300. All sections were scored, blinded and independently, by a clinical pathologist and a person with considerable training in histopathological scoring. Signals were considered positive when reaction products were localized in the expected cellular compartment.

6. Statistical Analysis

Comparisons of STC2 expression in 3 groups (Gleason score 2-6, 7 and 8-10) were analyzed using Kruskal-Wallis for multiple comparisons. $P<0.01$ were considered significant. Additional post-test was performed by using Mann-Whitney's U-test with Bonferroni method to adjust for multiple pair-wise differences. $P<0.003$ between 3 groups were considered significant with Bonferroni method. All statistical calculations were done with Statview software (ver. 5.0, SAS Institute Inc., North Carolina).

7. Construction of shRNA Expressing Vectors and Cell Viability Assay

To investigate the biological function of STC2 in PC cells, psiU6BX3.0 vector was used for expression of short hairpin RNA (shRNA) against a target gene as described previously (Tamura K, et al., Cancer Res 2007, 67, 5117-5125). Plasmids designed to express shRNA were prepared by cloning of double-stranded oligonucleotides into psiU6BX vector. The oligonucleotide sequences of target sequences for STC2 are as followed; sense strand sequence for
si1: 5'-CAACTCTTGTGAGATTCGG-3' (SEQ ID NO: 7),
si2: 5'-GACGAACAGTCTGAGTATT-3' (SEQ ID NO: 8),
si3: 5'-GCAGGAGCTGGTATTGTAG-3' (SEQ ID NO: 9), and
siEGFP: 5'-GAAGCAGCACGACTTCTTC-3' (SEQ ID NO: 10) as a negative control.

PC-3 cells ($2\times10^6$) which expressed STC2 in high level were seeded on 10-cm dishes, transfected with psiU6-STC2 (si1-3), or psiU6-siEGFP using FuGene6 (Roche) according to the manufacturer's instruction, and then cultured in appropriate medium containing 800 mcg/ml of Geneticin (Sigma-Aldrich) for 14 days. The cells were fixed with 100% methanol, stained with 0.1% of crystal violet-H20 for colony formation assay. In MTT assay, cell viability was measured using Cell-counting kit-8 (DOJINDO, Kumamoto, Japan) at 10 days after transfection. Absorbance was measured at 490 nm, and at 630 nm as reference, with a Microplate Reader 550 (Bio-Rad). Preliminarily, knockdown effects of these shRNA-expression vectors on endogenous STC2 expression were validated 7 days after transfection by RT-PCR using the primers used by semi-quantitative RT-PCR.

8. Generation of STC2-Overexpressing Cells and In-Vitro Growth Assay

Full-length human STC2 cDNA was amplified using primers that were designed to contain HA-tag sequences at the COOH terminus, and cloned into the pIRESneo3 vector (Clontech). Human PC cell line 22Rv1 cells were seeded into 100 mm-dish ($5\times10^5$ cells per a dish) and transfected with 6 micro gram of pIRESneo3 empty vector alone or pIRESneo3-STC2-HA expression vector using FuGENE6 reagent (Roche) according to the manufacturer's instructions. Cells were selected with appropriate medium containing 400 mcg/ml of Geneticin (Sigma-Aldrich) for 14 days when discrete colonies were isolated. All clones were maintained in selective medium. Each clone was assayed for STC2 protein expression by western blot analysis using anti-HA tag antibody (Roche). Proliferation of 22Rv1 cells that stably expressed STC2 (22Rv1-STC2) or those transfected with pIRESneo3 empty vector (22Rv1-mock clone mixture) were examined by Cell-counting kit-8 (DOJINDO, Kumamoto, Japan). Each of 22Rv1-STC2 and 22Rv1-mock cells was seeded at the concentration of $3\times10^3$ cells per well using 48-well plates. The assay was performed at every 48 hours for 9 days, according to the manufacturer's instruction.

Example 2

STC2 Over Expression in CRPC Cells

The genome-wide expression profiles of CRPC cells and CNPC cells purified from clinical PC tissues was previously reported (Tamura K, et al., Cancer Res 2007, 67, 5117-5125). Among a number of genes shown to be trans-activated in CRPC cells compared normal prostate epithelial cells (NP), STC2 was focused in this invention. Semi-quantitative RT-PCR (FIG. 1A) and real-time quantitative RT-PCR (FIG. 1B) confirmed the elevated expression of STC2 in 6 out of the 7 clinical CRPC cells, comparing with CNPC cells and NP cells. Northern blot analysis using five PC cell lines and normal adult tissues confirmed the elevated expression of STC2 in all of PC cell lines, compared with normal prostate and adult vital organs including brain, heart, kidney, liver, and lung, and testis (FIG. 1C). Multiple tissue northern (MTN) blot analysis also revealed no or very limited expression of STC2 in most normal adult organs, and low expression was observed only in normal pancreas (FIG. 1D).

Example 3

Immunohistochemical Analysis in Clinical PC Tissues

To validate the over-expression of STC2 protein in CRPC cells, immunohistochemical analysis on clinical PC tissues was performed by using monoclonal antibody specific to human STC2. As shown in FIG. 1E, strong immunochemical signal for STC2 was detected predominantly in the cytoplasm of cancer cells exceptionally in CRPC cases examined. 6 of 9 CRPCs examined showed strong immunoreactivity to anti-STC2 antibody and one CNPC with Gleason score 10 also showed strong immunoreactivity (FIG. 1F), while CNPC with Gleason score 7 did not show any immunoreactivity to anti-STC2 antibody (FIG. 1G). Adjacent normal prostatic epithelium in the same patient revealed very weak or no signal for STC2. Hormone ablation therapy is usually ineffective for PCs with Gleason score 10, which progress highly aggressively, and these findings demonstrated that STC2 was expressed specifically in CRPCs and highly aggressively PCs.

To further investigate the clinic-pathologic significance of STC2 expression in PC tissues, the relationship between the calculated immunohistochemical score for STC2 and Gleason score was analyzed. Since each PC specimen apparently showed a different degree of staining intensity and different proportion of the staining-positive cell, these heterogeneity were taken into consideration, and the immunohistochemical scoring system was applied; a combined weighed score was given by the sum of the proportion (0-100%) of stained cells for which the score 1, 2, or 3 was given according to the signal STC2 immunohistochemical scores and intensity as described previously (Ashida S, et al., Clin Cancer Res 2006, 2767-73). In comparison of STC2 expression, there were significant differences between Gleason score 2-6 group and 8-10 group, and between Gleason score 7 group and 8-10 group (Mann-Whitney's U-test with Bonferroni method, p=0.0006 and p=0.0004, respectively). No significant difference was observed between Gleason score 2-6 group and 7 group (p=0.0110). It was confirmed that STC2 immunohistochemical score revealed a strong correlation with high-grade PCs (Gleason score 8-10) (FIG. 1H, Table 1).

TABLE 1

Relationship between STC2 immunohistochemical score and Gleason score in CNPCs.

| Gleason score | STC2 immunohistochemical score | | |
|---|---|---|---|
| | n | Mean (SD) | *P |
| 2-6 | 12 | 113 (14) | |
| 7 | 33 | 123 (12) | |
| 8-10 | 8 | 194 (59) | *<0.003 |

Statistical significance was determined using Mann-Whitney's U-test with Bonferroni method.

Example 4

Knockdown of STC2 Expression by siRNA Attenuated PC Cell Growth

To examine biological roles of STC2 over-expression in PC cell, three vectors designed to express shRNA specifically to STC2 were constructed and transfected into PC cell lines PC-3, which expressed endogenous STC2 most strongly. Among the three shRNA-expression vectors, si2 and si3 showed the significant knockdown effect on endogenous STC2 transcript (FIG. 2A), and this transfection resulted in reduction of the numbers of colonies (FIG. 2B) as well as those of the viable cells measured by MTT assay for PC-3 cells (FIG. 2C). On the other hand, the transfection of si1 and a negative control (siEGFP) showed no or little knockdown effect on STC2 expression and did not affect cell viability of PC-3 cells. These findings indicated STC2 overexpression could play some important roles in PC cell growth or viability.

Example 5

STC2 Over-Expression Promoted Cancer Cell Growth

To further investigate for the potential oncogenic function of STC2, three stable transformants (Clones 1-3) were established from 22Rv1 cells, in which exogenous STC2 expressed constitutively. control 22Rv1 cells transfected empty vector (Mock) were also prepared and compared their proliferation. Western blot analysis (FIG. 2D) confirmed high level of exogenous STC2 expression in three stable clones (Clones 1-3). MTT assay showed that the three stable clone 1, 2 and 3 grew significantly more rapidly than the 22Rv1-mock clone mixture (*$P<0.01$, **$P<0.05$, Students't-test), indicating that STC2 over-expression promoted PC cell growth (FIG. 2E).

INDUSTRIAL APPLICABILITY

The present invention provides a novel target molecule or biomarker, STC2, for therapy development or diagnosis for PCs, especially for CRPCs and aggressive PCs. PC shows relatively good prognosis, and hormone-ablation therapy or castration is effective in most of relapsed or advanced PC. However, once CRPC cells emerge or it is at advanced stage with high Gleason score, there are very limited options for PC patient care, such as doxotaxel plus predonisone (Tannock I F, et al., N Engl J Med 2004, 351, 1502-12, and Petrylak D P, et al., N Engl J Med 2004, 351, 1513-20) which can still offer the minimum effect on PCs. Hence, it is most demanded to identify molecular targets for CRPCs or aggressive PCs and develop novel therapies for them to target those molecules. The examples described herein indicate restrictive expression of the STC2 gene in adult normal organs and critical roles of STC2 in PC cells. Therefore, STC2 is a promising target for a novel therapeutic approach with a minimal risk of adverse effects. More specifically, the expression of the STC2 gene is strongly related to CRPC cells viability. Thus, the detection and the inhibition of STC2 provide a novel effective therapeutic approach for a biomarker or a molecular treatment of CRPCs.

High-grade CNPCs, as well as CRPCs, respond poorly to androgen-ablation therapy and have highly aggressive behavior and poor prognosis. The immunohistochemical analysis described herein clearly indicates STC2 is over-expressed more strongly in high-grade CNPCs with Gleason score 8-10, as well as CRPC, than low-grade CNPCs. It was confirmed that STC2 immunohistochemical score revealed a strong correlation with Gleason score 8-10 (*$P<0.003$; FIG. 1H, Table 1). Thus, the detection and the inhibition of STC2 is also useful for predicting Gleason score of PC or treating aggressive PCs with high grade Gleason score (e.g., Gleason score 8-10).

STC2 is a secreted protein that functions to promote PC cell viability in autocrine/paracrine manner. Accordingly, it is possible to detect STC2 in patient serum, to thus serve as a diagnostic biomarker diagnosing PC (more suitably CRPC), or predicting PC aggressiveness and Gleason score, and neutlinization of STC2 by highly specific antibody have potential as one of the therapeutic strategies against PCs, in particular, CRPCs and aggressive PCs.

The data provided herein add to a comprehensive understanding of PCs, facilitate development of novel diagnostic strategies, and provide clues for identification of molecular targets for therapeutic drugs and preventative agents. Such information contributes to a more profound understanding of tumorigenesis, and provide indicators for developing novel strategies for diagnosis, treatment, and ultimately prevention of PCs.

All patents, patent applications, and publications cited herein are incorporated by reference in their entirety.

Furthermore, while the invention has been described in detail and with reference to specific embodiments thereof, it is to be understood that the foregoing description is exemplary and explanatory in nature and is intended to illustrate the invention and its preferred embodiments. Through routine experimentation, one skilled in the art will readily recognize that various changes and modifications can be made therein without departing from the spirit and scope of the invention. Thus, the invention is intended to be defined not by the above description, but by the following claims and their equivalents.

The invention claimed is:

1. A method for diagnosing prostate cancer in a subject, comprising the steps of:
   (a) determining the expression level of the stanniocalcin 2 (STC2) gene in a subject-derived prostate tissue wherein said expression level is determined by detecting a translation product of the STC2 gene;
   (b) comparing the subject-derived expression level determined in step (a) with a normal control level obtained from normal prostate epithelial cells; and
   (c) correlating an increase of said subject-derived expression level as compared to the normal control level to a diagnosis of prostate cancer.

2. The method of claim 1, wherein said prostate cancer is castration-resistant prostate cancer or aggressive prostate cancer.

3. The method of claim 2, wherein said aggressive prostate cancer is prostate cancer with Gleason score 8 to 10.

* * * * *